(12) United States Patent
Endo et al.

(10) Patent No.: US 10,457,698 B2
(45) Date of Patent: Oct. 29, 2019

(54) CHIRAL REAGENTS FOR PREPARATION OF SUBSTITUTED PHOSPHORODIAMIDATE MORPHOLINO OLIGOMERS

(71) Applicant: Eisai R&D Management Co., Ltd., Tokyo (JP)

(72) Inventors: Atsushi Endo, Andover, MA (US); Robert T. Yu, Arlington, MA (US); Francis Fang, Andover, MA (US); Hyeong Wook Choi, Andover, MA (US); Mingde Shan, Andover, MA (US)

(73) Assignee: Eisai R&D Management Co., Ltd, Tokyo (JP)

( * ) Notice: Subject to any disclaimer, the term of this patent is extended or adjusted under 35 U.S.C. 154(b) by 0 days.

(21) Appl. No.: 15/750,087

(22) PCT Filed: Aug. 5, 2016

(86) PCT No.: PCT/US2016/045876
§ 371 (c)(1),
(2) Date: Feb. 2, 2018

(87) PCT Pub. No.: WO2017/024264
PCT Pub. Date: Feb. 9, 2017

(65) Prior Publication Data
US 2018/0222932 A1 Aug. 9, 2018

Related U.S. Application Data

(60) Provisional application No. 62/201,510, filed on Aug. 5, 2015.

(51) Int. Cl.
| C07D 413/00 | (2006.01) |
| C07F 9/6561 | (2006.01) |
| C07F 9/6558 | (2006.01) |
| C07H 21/00 | (2006.01) |
| A61K 31/7088 | (2006.01) |

(52) U.S. Cl.
CPC ...... *C07F 9/65616* (2013.01); *A61K 31/7088* (2013.01); *C07F 9/65583* (2013.01); *C07H 21/00* (2013.01)

(58) Field of Classification Search
CPC .................................................. C07D 413/00
USPC ........................................................ 54/111
See application file for complete search history.

(56) References Cited

U.S. PATENT DOCUMENTS

| 5,185,444 A | 2/1993 | Summerton et al. |
| 2009/0131624 A1 | 5/2009 | Reeves et al. |
| 2012/0289457 A1 | 11/2012 | Hanson et al. |
| 2012/0296087 A1 | 11/2012 | Sinha et al. |
| 2013/0197220 A1 | 8/2013 | Ueda et al. |
| 2014/0330006 A1 | 11/2014 | Hanson et al. |

FOREIGN PATENT DOCUMENTS

| CN | 102702265 A | 10/2012 |
| EP | 1176151 A1 | 1/2002 |
| GB | 2357764 A | 7/2001 |
| WO | 9825944 A1 | 6/1998 |
| WO | 9938878 A1 | 8/1999 |
| WO | 2009064471 A1 | 5/2009 |
| WO | 2011150408 A2 | 12/2011 |
| WO | 2013082548 A1 | 6/2013 |
| WO | WO 17/024264 * | 2/2017 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Response to Rules 161(1) and 162 Communications in European App. No. 16767053.8 Having Common PCT Parent.

Paul, et al., "Synthesis and cell transfection properties of cationic uracil-morpholino tetramer," Jan. 29, 2014, Tetrahedron Lett., 55, 1072-76.

(Continued)

*Primary Examiner* — Douglas M Willis

(74) *Attorney, Agent, or Firm* — Buchanan Ingersoll & Rooney PC

(57) ABSTRACT

A method of preparation of stereospecific synthesis of diastereomerically pure phosphorodiamidate morpholino oligomers (PMOs) of one of the following general formulas is provided:

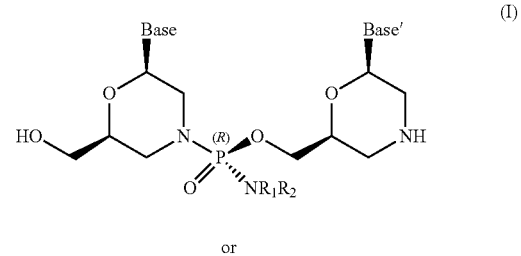

(I)

or

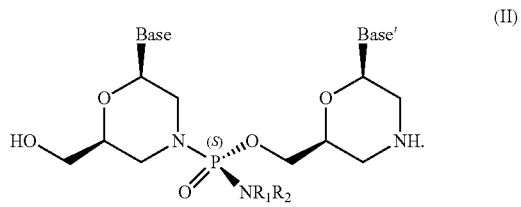

(II)

4 Claims, 11 Drawing Sheets
Specification includes a Sequence Listing.

(56) References Cited

OTHER PUBLICATIONS

Harakawa, et al., "Development of an Efficient Method for Phosphorodiamidate Bond Formation by Using Inorganic Salts," Feb. 1, 2012; Bioorg Med. Chem. Lett., 22(3); 1445-7.

Shestopalov, et al., "Light-controlled gene silencing in zebrafish embryos," Aug. 23, 2007, Nat. Chem. Bio., 3(10); 650-651. (With Supplementary Information).

Hall, et al., "Chiral OS-dialkyl phosphoramidothioates: their preparation, absolute configuration, and stereochemistry of their reactions in acid and base," Jan. 1, 1979; J. Chem. Soc., Perkin Transactions I, 1646-1655.

Enya, et al., "Chemical Synthesis of Diastereomeric Diadenosine Boranophosphates (ApbA) from 2'-O-(2-cyanoethoxymethyl)adenosine by the boranophosphotriester method," Oct. 15, 2008, Bioorg & Med. Chem. 16; 9154-9160.

Wan, et al., "Synthesis, biophysical properties and biological activity of second generation antisense oligonucleotides containing chiral phosphorothioate linkages," Nov. 14, 2014, 42 (22); Nuc. Acids Res., 13456-13468.

Third Party Observation in PCT/US2016/045876; Anonymous Author, submitted Jul. 28, 2017.

Response to Third Party Observation in PCT/US2016/045876; Applicant, submitted Jan. 19, 2018.

Colombian Office Action dated Mar. 5, 2018 (English Translation included).

International Search Report (PCT/ISA/210) dated Feb. 16, 2017, by the European Patent Office as the International Searching Authority for International Application No. PCT/US2016/045876.

Written Opinion (PCT/ISA/237) dated Feb. 16, 2017, by the European Patent Office as the International Searching Authority for International Application No. PCT/US2016/045876.

Summerton, et al., "Morpholino Antisense Oligomers: Design, Preparation, and Properties", Antisense & Nucleic Acid Drug Development, 1997, 187-195.

Summerton, "Morpholino antisense oligomers: the case for an RNase H-independent structural type", Biochimica et Biophysica Acta 1489, 1999, 141-158.

Written Opinion dated Jun. 11, 2019, by the Intellectual Property Office of Singapore (IPOS) in corresponding Singapore Patent Application No. 11201800967P. (6 pages).

Office Action dated Jul. 10, 2019, by the Chilean Patent Office in corresponding Chilean Patent Application No. 201800322 and an English Translation of the Office Action. (23 pages).

\* cited by examiner

FIG. 1

Resolution of Diastereomers of Activated Monomers and Stereospecific PMO Coupling Ten Key "Reagents" to Construct Homogeneous Oligomers New Method Provides Direct Access to Stereopure (Homogeneous) PMOs

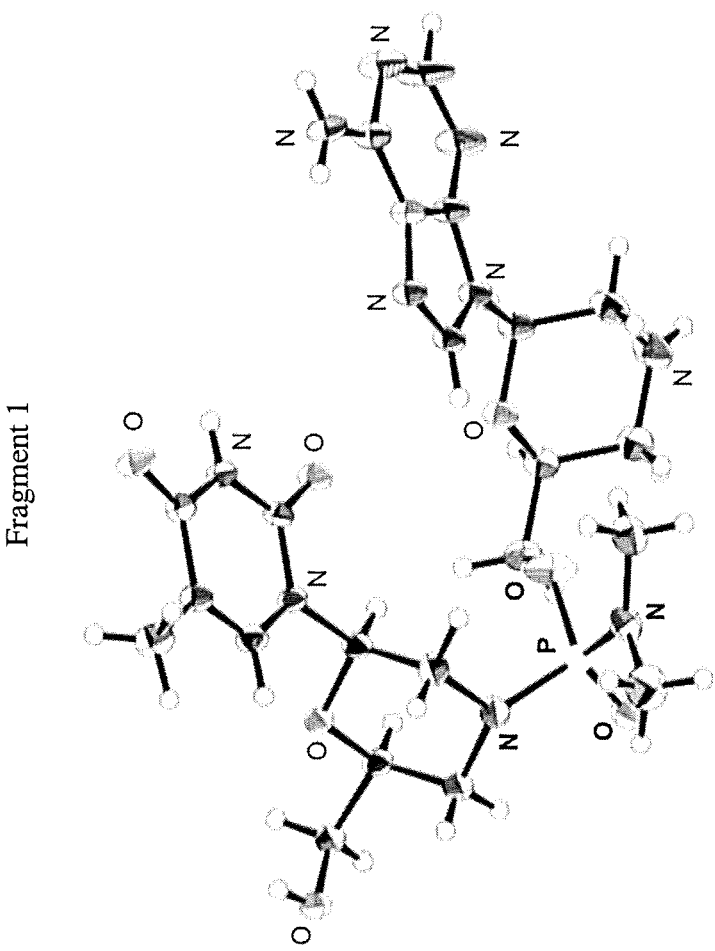
FIG. 9A Fragment 1

Fragment 2

CHIRAL REAGENTS FOR PREPARATION OF SUBSTITUTED PHOSPHORODIAMIDATE MORPHOLINO OLIGOMERS

CROSS-REFERENCE TO RELATED APPLICATIONS

This application claims priority to U.S. Provisional Patent Application No. 62/201,510, filed on Aug. 5, 2015. That application is incorporated by reference herein.

BACKGROUND

Field

Embodiments may relate to preparation of substantially diastereomerically pure activated monomers that are phosphoramidochloridate morpholino subunits. Embodiments may also relate to use of substantially diastereomerically pure activated phosphorylated morpholino monomers for preparation of molecules through stereospecific coupling reactions.

Background

Synthesis of diastereomerically pure phosphorodiamidate oligonucleotides is substantially complicated by the existence of chiral phosphorous linkages. This is contrasted with, for example, phosphodiester linkages, which do not have a chiral phosphorous. Examples may be seen in FIG. 1, which compares phosphodiester, phosphorothioate (which also includes a chiral phosphorous), and phosphorodiamidate The existence of the chiral phosphorous presents substantial challenges to synthetic routes that involve connection of a series of phosphorodiamidate nucleotides. Lack of stereochemically pure reagents (templates, subunits, building blocks) that enable stereospecific formation of phosphorodiamidate linkages leads to reaction at the stereocenter in which the phosphorus chirality of the resulting compound may not be controlled.

As shown graphically in FIG. 2, the use of diastereomeric mixtures of nucleotides for stereochemically uncontrolled coupling to prepare an oligonucleotide of any significant length and sequence creates a heterogeneous mixture of many diastereomers. The number of diastereomers is theoretically $2^{(n-1)}$, where n is the number of nucleotides that are connected to form the oligonucleotide. As shown in FIG. 2, even a modest four-nucleotide oligonucleotide (tetranucleotide) can result in formation of a mixture of eight separate diastereomers.

Formation of a significant number of diastereomers can create the need for sensitive separation techniques following synthesis. Yield of desired product may be adversely impacted by use of raw materials to prepare multiple diastereomers that are not desired.

It would be useful to be able to select a specific diastereomer prior to synthesis, then to synthesize the selected diastereomer in a stereochemically pure or substantially-pure form.

BRIEF SUMMARY

Embodiments may provide one or more stereochemically pure or substantially stereochemically pure compounds of Table 1. Further embodiments may also provide enantiomers of the compounds of Table 1. Typically the stereochemistry of those enantiomers varies from that of the compounds of Table 1 by the alteration of the stereochemistry of the morpholino ring.

TABLE 1

| Compound | Formula # |
|---|---|
| (structure) | 20 |
| (structure) | 21 |
| (structure) | 22 |
| (structure) | 23 |

TABLE 1-continued

| Compound | Formula # |
|---|---|
| (structure: adenine with NHR5, morpholine ring with N-R3, phosphoramidate with Cl, O, NR1R2) | 24 |
| (structure: adenine with NHR5, morpholine ring with N-R3, phosphoramidate with Cl, O, NR1R2) | 25 |
| (structure: guanine with NHR6, morpholine ring with N-R3, phosphoramidate with Cl, O, NR1R2) | 26 |
| (structure: guanine with NHR6, morpholine ring with N-R3, phosphoramidate with Cl, O, NR1R2) | 27 |
| (structure: thymine with Me, morpholine ring with N-R3, phosphoramidate with Cl, O, NR1R2) | 28 |

TABLE 1-continued

| Compound | Formula # |
|---|---|
| (structure: thymine with Me, morpholine ring with N-R3, phosphoramidate with Cl, O, NR1R2) | 29 |
| (structure: purine with OR9 and NHR6, morpholine ring with N-R3, phosphoramidate with Cl, O, NR1R2) | 30 |
| (structure: purine with OR9 and NHR6, morpholine ring with N-R3, phosphoramidate with Cl, O, NR1R2) | 31 |

$R_1$ and $R_2$ may be the same or different, and may be —H, optionally substituted C1-C3 alkyl, optionally substituted phenyl, optionally substituted naphthyl, or, with the nitrogen to which they are attached, form an optionally substituted heterocycle, which may be, for example, pyrrolidine, piperazine, or morpholine.

Optionally substituted moieties may be substituted with one or more of methyl, ethyl, halogen, nitro, methoxy, or cyano.

$R_3$ may be trityl (Tr), which may be substituted trityl, including but not limited to such as MMTr (p-methoxyphenyldiphenylmethyl), optionally substituted benzyl, 4-methoxybenzyl (PMB, MPM), 3,4-dimethoxybenzyl, diphenylmethyl (Dpm), or sulfonyl, which may be a cleavable sulfonyl. In some embodiments, sulfonyl is 2-nitrobenzenesulfonyl, 4-nitrobenzenesulfonyl, or 2,4-dinitrobenzenesulfonyl.

$R_4$, $R_5$, $R_6$ may be —H, —C(O)R$_7$, or —C(O)OR$_7$, where $R_7$ is alkyl (methyl, ethyl, isopropyl, or other C1-C6 alkyl), benzyl, 2,2,2-trichloroethyl, or aryl (including but not limited to phenyl, 4-methoxy phenyl, 4-bromophenyl, and 4-nitrophenyl). $R_9$ may be optionally substituted alkyl, cyanoethyl, acyl, carbonate, carbamate, optionally substituted benzyl, 4-pivaloyloxy benzyl, and silyl.

In further embodiments, morpholino nucleosides in addition to those shown in Table 1 may be prepared in diastereomerically pure or substantially diastereomerically pure form.

Embodiments may also provide methods for separation of diastereomeric mixtures of the above-disclosed compounds into stereochemically pure or substantially stereochemically pure compounds. Further embodiments may provide pharmaceutical compositions comprising stereochemically pure or substantially stereochemically pure compounds as reported herein. Further embodiments may provide pharmaceutical compositions comprising pharmaceutically acceptable salts of stereochemically pure or substantially stereochemically pure compounds as reported herein. Pharmaceutical compositions may be administered in effective amounts to patients in need of treatment. Pharmaceutical compositions may further include pharmaceutically acceptable carriers.

In some embodiments the following moiety in each of the compounds of Table 1 may be substituted at positions a, b, and e with one or two methyl groups, and may be substituted at positions c and d with one methyl group. In each case the methyl group may be oriented on either side of the plan of the morpholino ring. In further embodiments, an additional methylene, optionally substituted with one or more methyl groups, may be inserted adjacent to the nitrogen in the morpholino group to allow for expansion to a seven-membered ring.

Embodiments further provide for preparation of stereochemically pure oligonucleotides through stereospecific coupling of activated monomers. Further embodiments provide substantially diastereomerically pure oligomer made by stereospecific coupling of activated monomers. Still further embodiments provide substantially diastereomerically pure compositions comprising substantially diastereomerically pure compounds as reported herein.

DESCRIPTION OF THE SEVERAL VIEWS OF THE DRAWINGS

Figure 1:
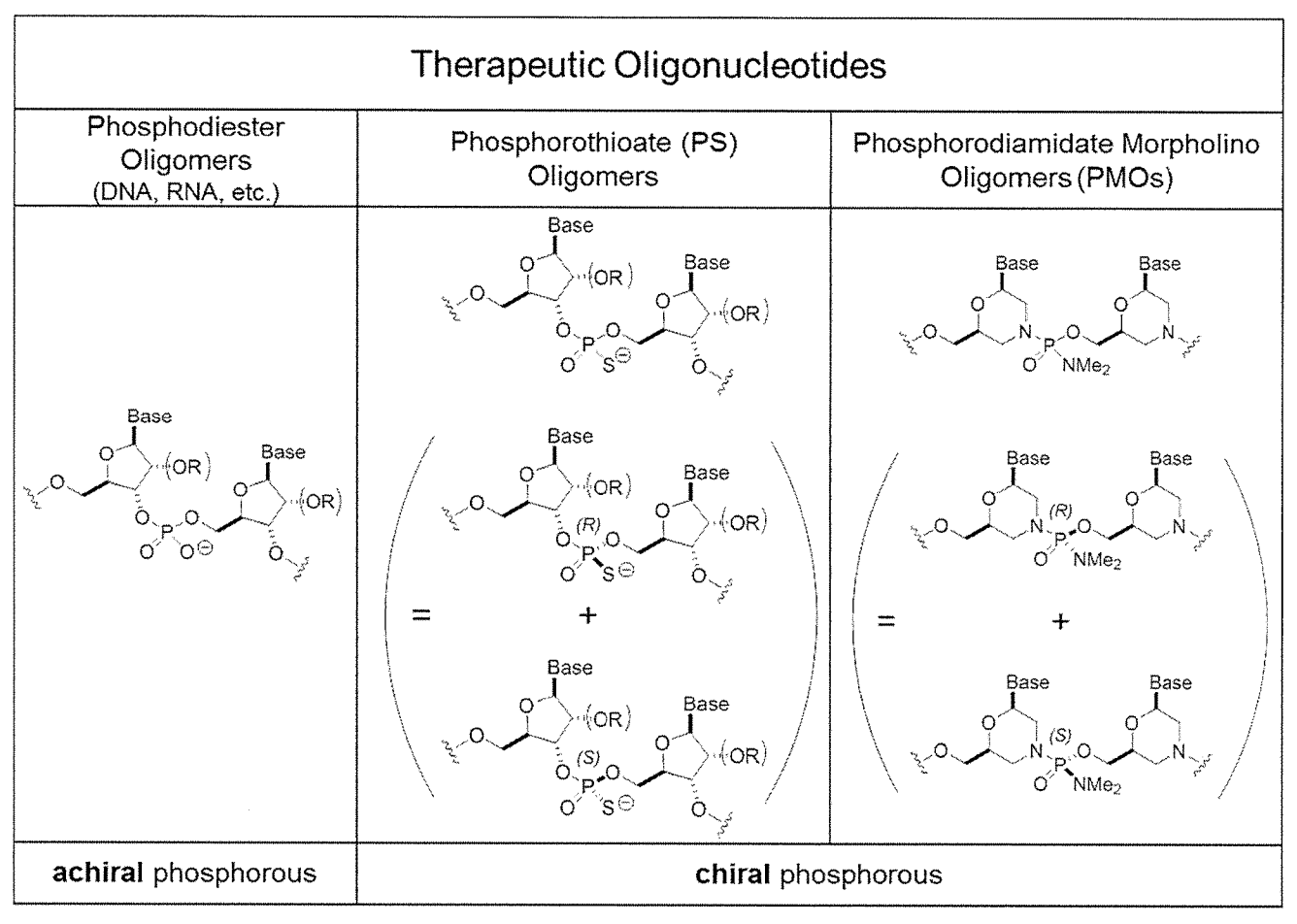

FIG. 1 shows phosphodiester, phosphorothioate, and phosphorodiamidate oligonucleotide linkages.

FIG. 2 also shows the proliferation of diastereomers that typically results when diastereomeric mixtures of phosphorodiamidate oligomer precursors are used to synthesize dinucleotides (2-mers), trinucleotides (3-mers), tetranucleotides (4-mers), and N-mers.

FIG. 9A and FIG. 9B show ORTEP plots of two fragments of Compound 100, as reported below.

DETAILED DESCRIPTION

Figure 2:
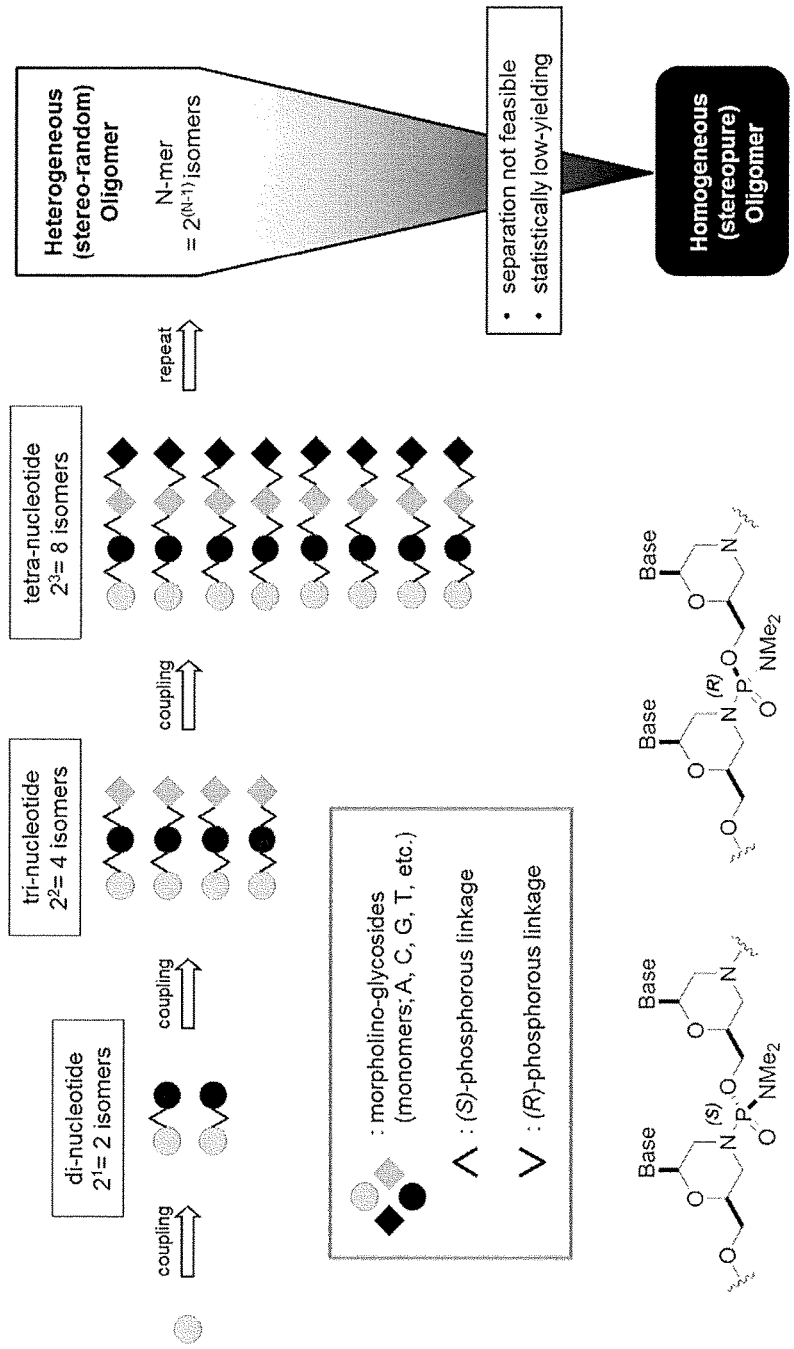
FIG. 2 shows the R- and S-phosphorous linkages in a phosphorodiamidate morpholino oligomer (PMO).
Figure 3:
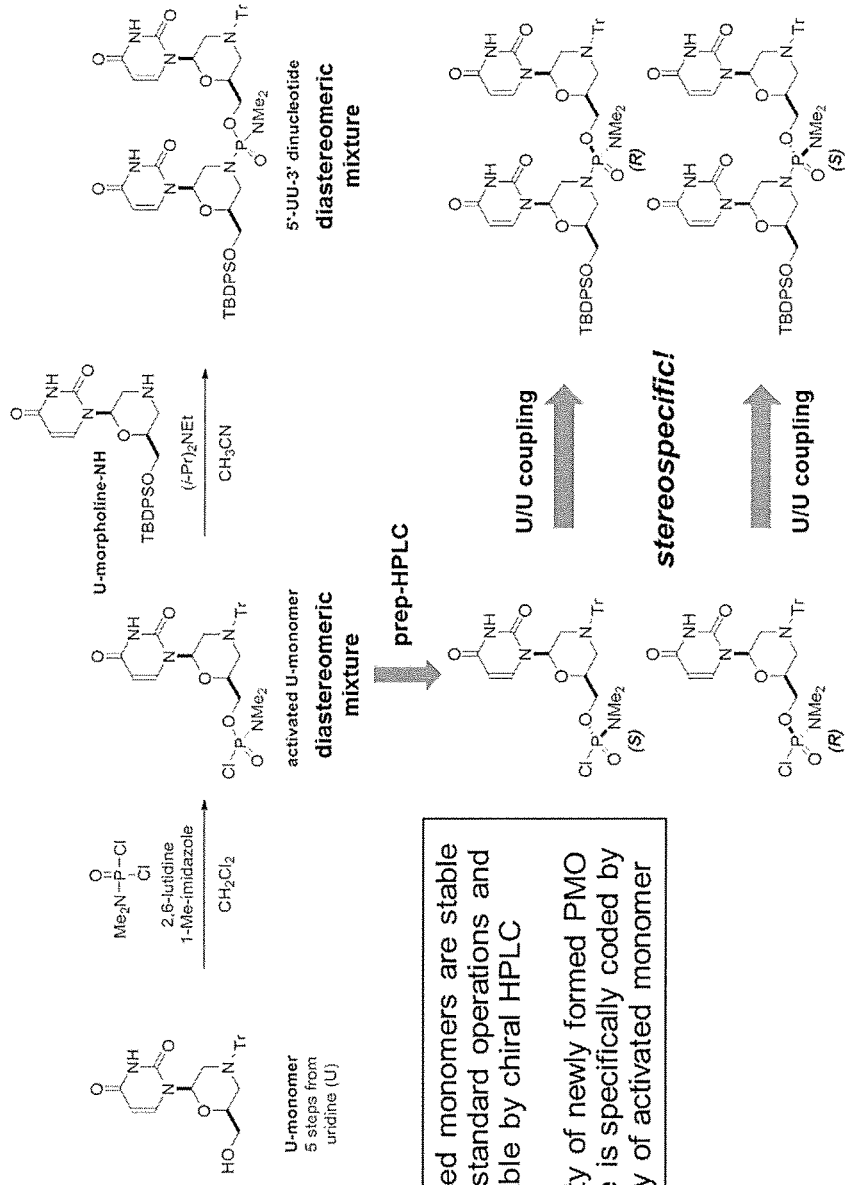
FIG. 3 shows preparation of diastereomerically pure dinucleotides both by using diastereomerically pure phosphoramidochloridates and by using diastereomeric mixture of phosphoramidochloridates.
Figure 4A:
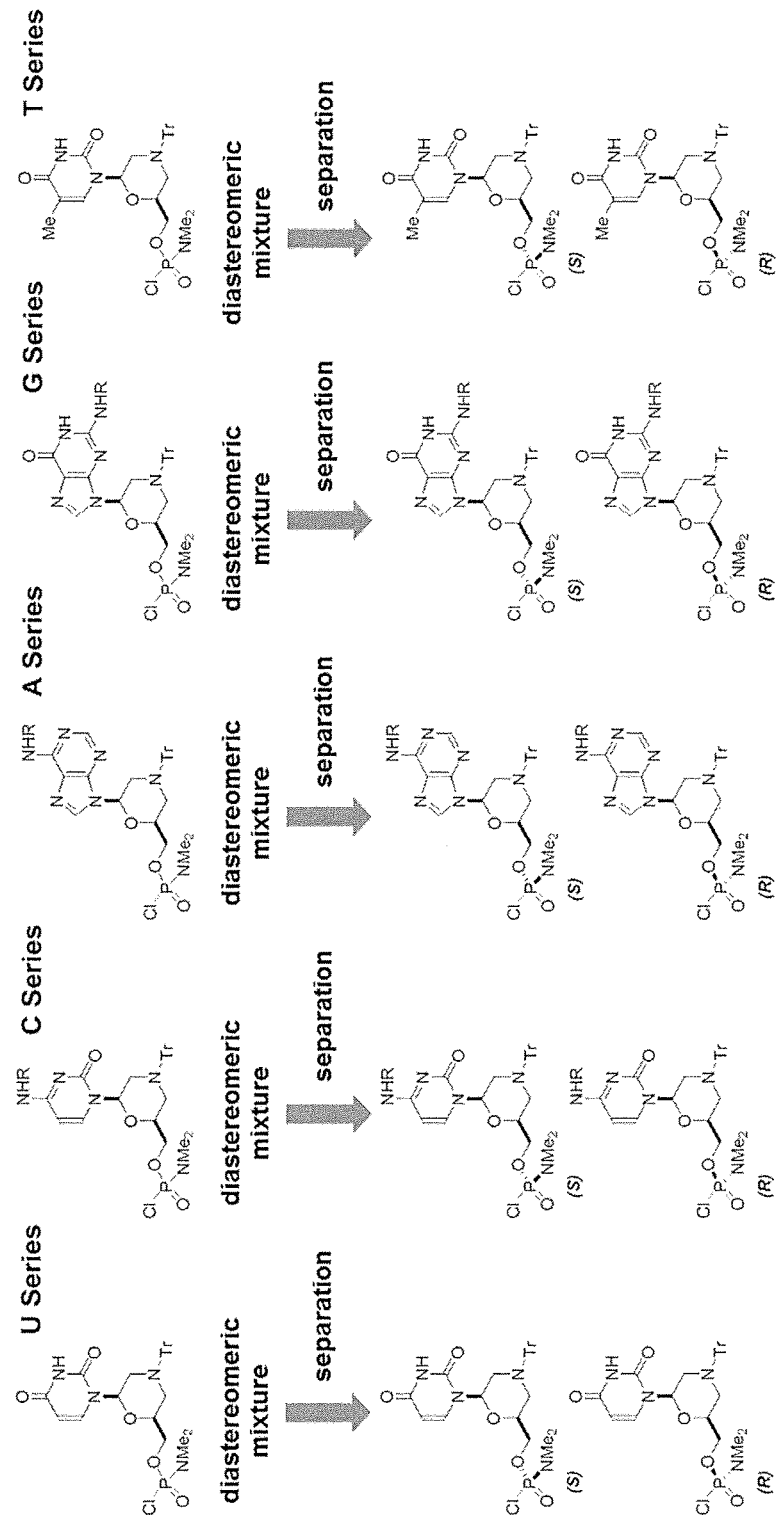
FIG. 4A and FIG. 4B show generalized diastereomeric mixtures of phosphoramidochloridates that may be useful for preparation of diastereomerically pure or substantially diastereomerically pure diastereomeric subunits.
Figure 4B:
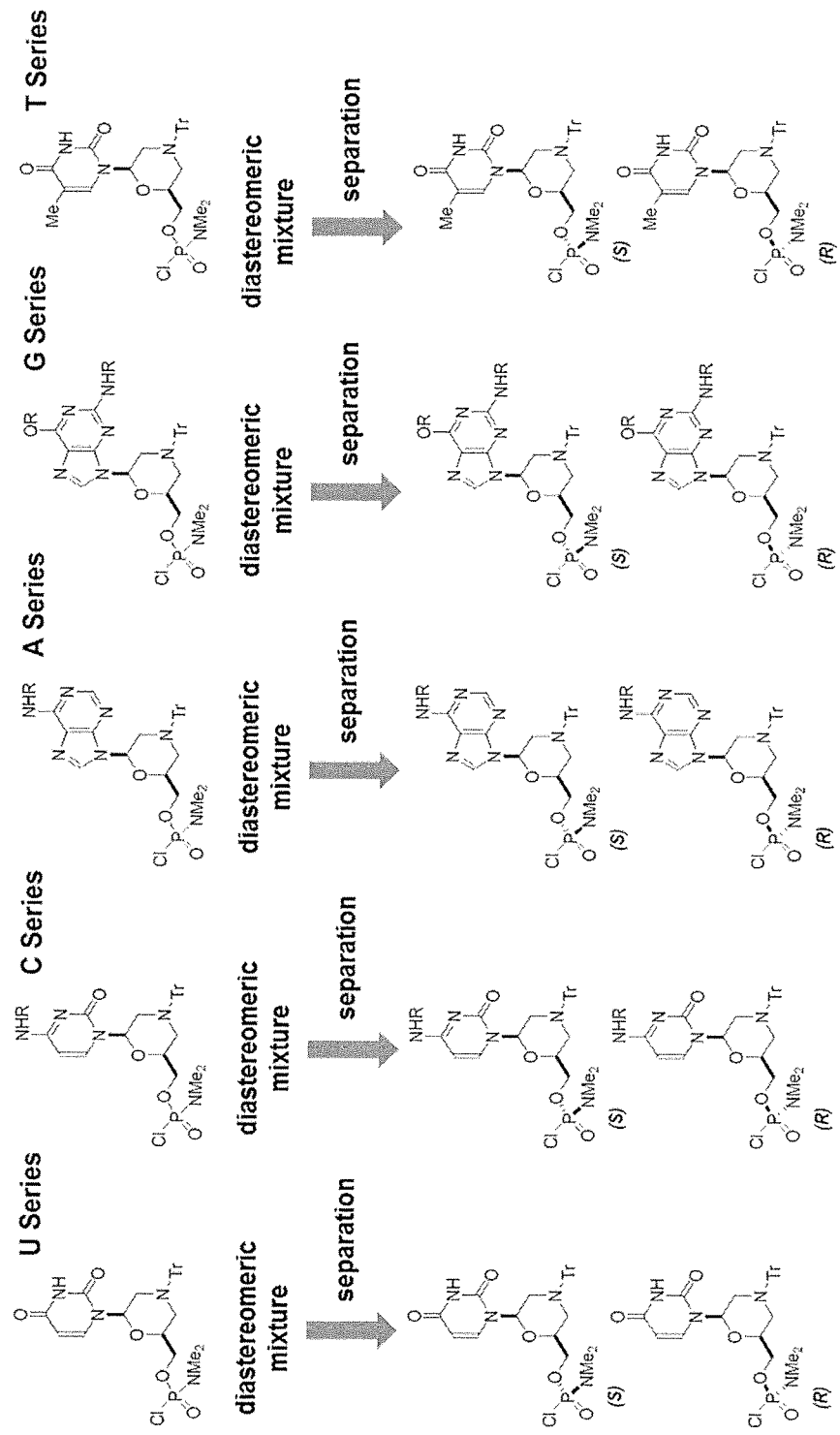
Figure 5:
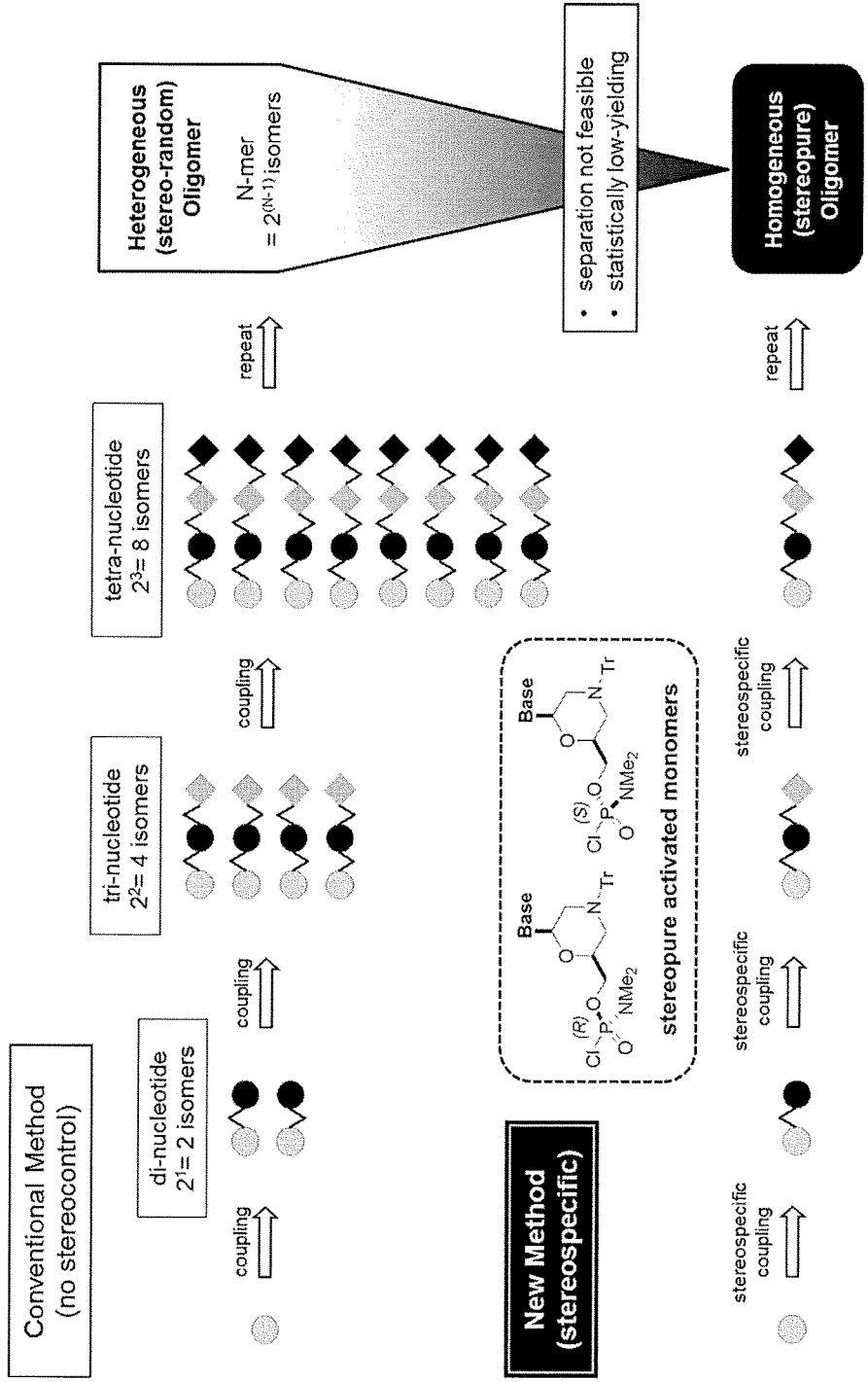
FIG. 5 shows preparation of diastereomerically pure (homogeneous) oligonucleotides using diastereomerically pure phosphoramidochloridates as reported herein.

We have found that two diastereomers of activated morpholino subunits may be sorted by their physical properties, allowing preparation of diastereometrically pure isomers. This permits preparation of stereochemically pure or substantially stereochemically pure PMOs under controlled reaction conditions, which may then be used to selectively prepare oligonucleotides with a desired stereochemistry.

Embodiments may also provide methods for separation of diastereomeric mixtures of the above-disclosed compounds into stereochemically pure or substantially stereochemically pure compounds. Once separated, the pure diastereomers from the formerly diastereomeric mixture may be used to prepare diastereomerically pure compounds through stereospecific coupling reactions.

Diastereomerically pure compounds and substantially diastereomerically pure compounds prepared as set forth herein may be diastereomerically pure phosphorodiamidate oligonucleotides. These diastereomerically pure and substantially diastereomerically pure phosphorodiamidate oligonucleotides may have multiple uses. For example, they may be useful as pharmaceuticals. They may be selected for properties that are potentially superior to those of heterogeneous mixtures (stereo-random mixtures) of diastereomers of phosphorodiamidate oligonucleotides. For example, they may be selected for differences in potency, efficacy, stability, safety, and specificity. Diastereomerically pure and substantially diastereomerically pure oligomers may have physical, chemical, and biological properties that differ from those of stereochemically heterogeneous mixtures of oligomers.

"Stereoisomers" refers to isomers that differ only in the arrangement of the atoms in space.

"Diastereomers" refers to stereoisomers that are not mirror images of each other.

"Enantiomers" refers to stereoisomers that are non-superimposable mirror images of one another. Enantiomers include "enantiomerically pure" isomers that comprise substantially a single enantiomer, for example, greater than or equal to 90%, 92%, 95%, 98%, or 99%, or equal to 100% of a single enantiomer.

"Activated monomer" refers to 5'-O-phosphorylated morpholino subunits that bear reactive phosphorous having leaving groups, including but not limited to chloride and halide leaving groups, that undergo displacement reaction with nucleophiles, including but not limited to amines and alcohols.

"R" and "S" as terms describing isomers are descriptors of the stereochemical configuration at asymmetrically substituted atoms, including but not limited to: carbon, sulfur, phosphorous and ammonium nitrogen. The designation of asymmetrically substituted atoms as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

An enantiomer can be characterized by the direction in which it rotates the plane of plane polarized light, as is well known to those in the chemical arts. If it rotates the light clockwise (as seen by a viewer towards whom the light is traveling), that enantiomer is labeled (+), and is denoted dextrorotatory. Its mirror-image will rotate plane polarized light in a counterclockwise direction, and is labeled (−), or levorotatory. The direction of rotation of plane polarized light by an enantiomerically pure compound, termed the sign of optical rotation, may be readily measured in standard device known as a polarimeter.

"Racemic" refers to a mixture containing equal parts of individual enantiomers.

"Non-racemic" refers to a mixture containing unequal parts of individual enantiomers. A non-racemic mixture may be enriched in the R- or S-configuration, including, without limitation, about 50/50, about 60/40, and about 70/30 R- to S-enantiomer, or S- to R-enantiomer, mixtures.

"Substantially stereochemically pure" and "substantial stereochemical purity" refer to enantiomers or diastereomers that are in enantiomeric excess or diastereomeric excess, respectively, equal to or greater than 80%. In some embodiments, "Substantially stereochemically pure" and "substantial stereochemical purity" refer to enantiomers or diastereomers that are in enantiomeric excess or diastereomeric excess, respectively, equal to or greater than 87%, equal to or greater than 90%, equal to or greater than 95%, equal to or greater than 96%, equal to or greater than 97%, equal to or greater than 98%, or equal to or greater than 99%. "Substantially Diastereomerically Pure" refers to diastereomers that are in diastereomeric excess equal to or greater than 87%, equal to or greater than 90%, equal to or greater than 95%, equal to or greater than 96%, equal to or greater than 97%, equal to or greater than 98%, or equal to or greater than 99%.

"Enantiomeric excess" (ee) of an enantiomer is [(the mole fraction of the major enantiomer) minus the (mole fraction of the minor enantiomer)]×100. Diastereomeric excess (de) of a diastereomer in a mixture of two diastereomers is defined analogously.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like.

An "effective amount" of a combination of therapeutic agents (e.g., Compound 1 and a CDK 4/6 inhibitor) is an amount sufficient to provide an observable therapeutic benefit compared to HCC or IHCC left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

Embodiments of the invention provide for preparation of stereochemically pure isomers or substantially stereochemically pure isomers, followed by use of the pure isomers to stereospecifically prepare diastereomerically pure phosphorodiamidate morpholino oligomers (PMOs). Preparation may be by separation of the diastereomeric mixture of phosphoramidochloridate nucleotides. Separation may be made by, for example, chromatography; for example, high performance liquid chromatography or "HPLC." Separation may also be accomplished through crystallization.

Separated monomers may be referred to as "active" monomers. By "active" it is meant that the monomers include phosphoramidochloridate moiety that is reactive towards a variety of nucleophiles, which include but not limited to: amines, alcohols/alkoxides, thiol/thiolate, alkyllithium, and Grignard reagents.

I. Preparation of Diastereometric Isomers

In one embodiment, stereochemically pure or substantially stereochemically pure activated monomers may be prepared by separation of a diastereomeric mixture of monomers. Separation may be accomplished by methods that permit distinction of stereoisomers using physical properties. For example, separation may be accomplished through chromatography or crystallization. Suitable types of chromatography include, for example, but are not limited to high performance liquid chromatography (HPLC), simulated moving bed chromatography, countercurrent chromatography, and other types of separative chromatography. For example, a diastereomeric mixture may be subjected to HPLC, eluting a fast-moving fraction and a slow-moving fraction. Each of these fractions is a different stereochemically pure or substantially stereochemically pure amount of a monomer. As described below, these monomers may be used to prepare oligomers with desired stereochemistry through stereospecific coupling using controlled reaction conditions.

We have further determined that, once separated, the stereochemically pure activated monomers have sufficient stability for use in further chemical reactions. Furthermore, we have determined that the stereochemically pure activated monomers can undergo stereospecific chemical reactions. Thus, as discussed in more detail below, these stereochemically pure activated monomers may be used for stereospecific coupling reactions to prepare stereochemically pure products.

As noted above, embodiments may provide one or more stereochemically pure or substantially stereochemically pure compounds of Table 1, which may be prepared by taking advantage of different physical properties in the stereoisomers. Further embodiments may also provide enantiomers of the compounds of Table 1. Typically the stereochemistry of those enantiomers varies from that of the compounds of Table 1 by the alteration of the stereochemistry of the morpholino ring.

TABLE 1

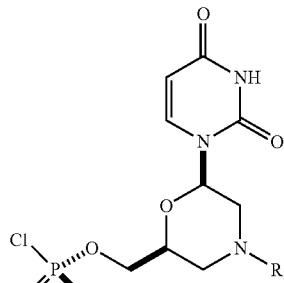

TABLE 1-continued

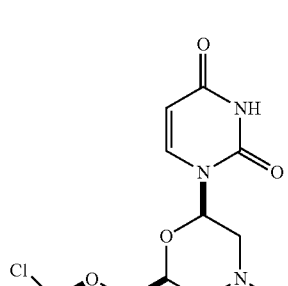

TABLE 1-continued

| Compound | Formula # |
|---|---|
| (structure: guanine-morpholino with P(=O)(Cl)(NR₁R₂), R₃ on N) | 27 |
| (structure: thymine-morpholino with P(=O)(Cl)(NR₁R₂), R₃ on N) | 28 |
| (structure: thymine-morpholino with P(=O)(Cl)(NR₁R₂), R₃ on N) | 29 |
| (structure: OR₉-purine-NHR₆ morpholino with P(=O)(Cl)(NR₁R₂), R₃ on N) | 30 |
| (structure: OR₉-purine-NHR₆ morpholino with P(=O)(Cl)(NR₁R₂), R₃ on N) | 31 | wherein R3 is optionally substituted triphenylmethyl (also referred to as "trityl"), optionally substituted benzyl, or sulfonyl. R4, R5, and R6 may be —C(O)R7 or —C(O)OR8, where R7 is methyl, ethyl, or phenyl, and R8 is benzyl or 2,2,2-trichloroethyl. R may be optionally substituted alkyl, cyanoethyl (for use as a protecting group see, for example, U.S. Patent Application Pub. No. US2013/0197220), acyl, sulfonyl, acetal/ketal, carbonate, carbamate, optionally substituted benzyl, 4-pivaloyloxy benzyl, and silyl.

In some embodiments, the optionally substituted benzyl is 4-methoxybenzyl (PMB, MPM). In some embodiments, sulfonyl is a cleavable sulfonyl. In some embodiments, sulfonyl is 2-nitrobenzenesulfonyl, 4-nitrobenzenesulfonyl, or 2,4-dinitrobenzenesulfonyl.

R1 and R2 may be the same or different, and may be —H, optionally substituted C1-C3 alkyl, optionally substituted phenyl, optionally substituted naphthyl, or, with the nitrogen to which they are attached, form an optionally substituted heterocycle, which may be, for example, pyrrolidine, piperazine, or morpholine.

Optionally substituted moieties may be substituted with one or more of methyl, ethyl, halogen, nitro, or cyano.

R3 may be trityl (Tr), which may be substituted trityl, including but not limited to such as MMTr (p-methoxyphenyldiphenylmethyl), benzyl, 4-methoxybenzyl (PMB, MPM), and 3,4-dimethoxybenzyl, diphenylmethyl (Dpm), R4, R5, R6 may be —H, —C(O)R7, or —C(O)OR7, where R7 is alkyl (methyl, ethyl, isopropyl, or other C1-C6 alkyl) or aryl (including but not limited to phenyl, 4-methoxy phenyl, 4-bromophenyl, and 4-nitrophenyl).

II. Stereospecific Coupling

In addition to determining that separation technology might be used to prepare substantially stereochemically pure amounts of activated monomer, we have determined that these activated monomers may, under some reaction conditions, be used to accomplish stereospecific coupling for the preparation of stereochemically pure dinucleotides, stereochemically pure trinucleotides, and larger stereochemically pure oligomers. Through use of methods reported herein, chirality of newly formed PMO linkage may be specifically coded by chirality of stereochemically pure active monomers used to form the oligomer.

Typical reaction conditions for stereospecific coupling include reaction in aprotic solvents. These solvents may be, for example, but are not limited to, acetonitrile, tetrahydrofuran (THF), 1,3-dimethylimidazolidinone (DMI), dimethylformamide (DMF), N-methyl-2-pyrrolidinone (NMP), dimethylacetamide (DMAc), dichloromethane (DCM), 1,2-dichloroethane (DCE), chloroform, 1,4-dioxane, ethyl acetate, 2-methyltetrahydrofuran, and isopropyl acetate. Coupling reactions may be conducted in the presence of non-nucleophilic tertiary amine bases and aromatic bases. Suitable bases include, but are not limited to, diisopropylethylamine, triethylamine, 2,6-lutidine, trimethylpyridines (collidines), and N-ethylmorpholine. Reaction temperatures may range from room temperature (about 20° C.) to 50° C. Sonication may be applied in some cases to help dissolution of substrate(s).

To demonstrate the feasibility of stereospecific coupling, multiple substantially stereochemically pure PMO dinucleotides were prepared by stereospecific PMO coupling of the fast- and slow-eluting substantially stereochemically pure active monomers (phosphoramidochloridates). Table 2, below, summarizes HPLC retention profiles of these substantially stereochemically pure PMO dinucleotides The table compares retention times for dinucleotides that were prepared from combinations of the 5'-end monomers listed on the left of the table with both faster-eluting and slower-eluting isomers of 3'-end monomers listed on the top. The table demonstrates that stereospecific coupling of substantially stereochemically pure active monomers produces different diastereomerically pure dinucleotides having different physical properties.

TABLE 2

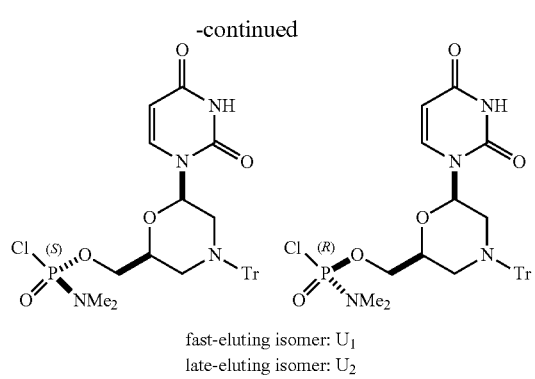

Active Monomers (3'-end; electrophiles)

| | | | U | | C[c] | | A[d] | | G[b] | | T | | |
|---|---|---|---|---|---|---|---|---|---|---|---|---|---|
| | | | fast U₁ | slow U₂ | fast C₁ | slow C₂ | fast A₁ | slow A₂ | fast G₁ | slow G₂ | fast T₁ | slow T₂ | |
| Base | U | UU₁ 9 < | UU₂ 27 | UC₁ 9.1 > | UC₂ 6.5 | UA₁ 12.6 > | UA₂ 10.9 | UG₁ 12.5 < | UG₂ 18.8 | UT₁ 8.4 < | UT₂ 27 | dinucleotide RT (min) |
| (5'-end monomers (nucleophiles)) structure: TBDPSO-morpholine-NH | C[a] | CU₁ 5.6 < | CU₂ 6.6 | CC₁ 6.7 > | CC₂ 5.7 | CA₁ 8 > | CA₂ 7.4 | CG₁ 10.4 < | CG₂ 13.3 | CT₁ 5.6 < | CT₂ 6.1 | dinucleotide RT (min) |
| | A[a] | AU₁ 3.5 < | AU₂ 3.6 | AC₁ 3.6 = | AC₂ 3.6 | AA₁ 4.2 > | AA₂ 4.1 | AG₁ 7.6 < | AG₂ 8.5 | AT₁ 3.5 < | AT₂ 3.6 | dinucleotide RT (min) |
| | G[b] | GU₁ 7.6 < | GU₂ 8.1 | GC₁ 7.2 = | GC₂ 7.2 | GA₁ 9.7 > | GA₂ 8.9 | GG₁ 14.2 > | GG₂ 11.3 | GT₁ 7.4 < | GT₂ 7.5 | dinucleotide RT (min) |
| | T | TU₁ 9.7 < | TU₂ 23.9 | TC₁ 8.9 > | TC₂ 5.6 | TA₁ 13.2 > | TA₂ 11.4 | TG₁ 13.2 < | TG₂ 20.0 | TT₁ 9 < | TT₂ 24 | dinucleotide RT (min) |

[a] nucleobases unprotected
[b] guanine amino group protected with isobutyryl group
[c] cytosine amino group protected with: (1) acetyl group for coupling with U, C, A and G, (2) benzoyl group for coupling with T
[d] adenine amino group protected with benzoyl group Analytical HPLC conditions for profiling of the substantially stereochemically pure PMO dinucleotides of Table 2 are reported below:

| HPLC column | Chiralpak IC 4.6 × 250 mm 5 μm |
|---|---|
| Temperature | 30° C. |
| Flow rate | 1.0 mL/min |
| Mobile phase | 10% n-heptane, 80% EtOAc and 10% MeOH—EtOH 1:1 with 0.1% diethylamine |
| Gradient | Isocratic |
| Run time | 30 min |
| Injection volume | 1-2 μL (0.2 mg/ml, dichloromethane) |
| Detection | UV 260 nm |

EXAMPLES

III. Examples of Diastereomeric Separation of Activated Monomers

The following examples show diastereomer separation of activated monomers according to certain embodiments as presented herein.

A. U-Monomers

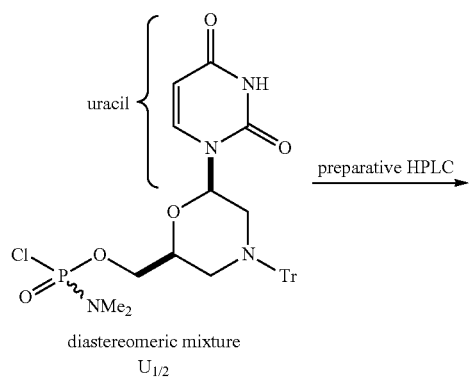

diastereomeric mixture U₁/₂ preparative HPLC → fast-eluting isomer: U₁
late-eluting isomer: U₂

Analytical HPLC Conditions for Activated U Monomers:

| HPLC column | Chiralpak IC, 4.6 × 250 mm, 5 u |
|---|---|
| Temperature | 35° C. |
| Flow rate | 1 mL/min |
| Mobile phase | Ethyl acetate |
| Gradient | Isocratic |
| Run time | 15 min |
| Injection volume | 10 μL (5 mg/ml, ethyl acetate) |
| Detection | 260 nm |
| Retention Time | U₁    5 min |
| | U₂    7.5 min |

Preparative HPLC Conditions for Activated U Monomers:

Chiralpak IC, 21×250 mm, 5μ; Elute column at 11 ml/minute with ethyl acetate, room temperature, 260 nm detection.

[$^1$H-NMR data for U₁]

$^1$H NMR (400 MHz, CDCl₃) δ 8.18 (br, 1H), 7.45 (m, 6H), 7.15-7.32 (m, 10H), 6.12 (dd, 1H, J=2.0 & 9.6 Hz), 5.62 (d, 1H, J=8.0 Hz), 4.39 (m, 1H), 4.11 (m, 2H), 3.39 (d, 1H, J=11 Hz), 3.15 (d, 1H, J=11 Hz), 2.65 (s, 3H), 2.62 (s, 3H), 1.49 (t, 1H, J=11 Hz), 1.39 (t, 1H, J=11 Hz)

[¹H-NMR data for U₂]

¹H NMR (400 MHz, CDCl₃) δ 8.07 (br, 1H), 7.44 (m, 6H), 7.14-7.34 (m, 10H), 6.12 (dd, 1H, J=2 & 9 Hz), 5.61 (d, 1H, 8.0 Hz), 4.39 (m, 1H), 4.08 (m, 2H), 3.39 (d, 1H, J=12 Hz), 3.15 (d, 1H, J=12 Hz), 2.66 (s, 3H), 2.62 (s, 3H), 1.46 (t, 1H, J=11 Hz), 1.38 (t, 1H, J=11 Hz),

B. A-Monomers

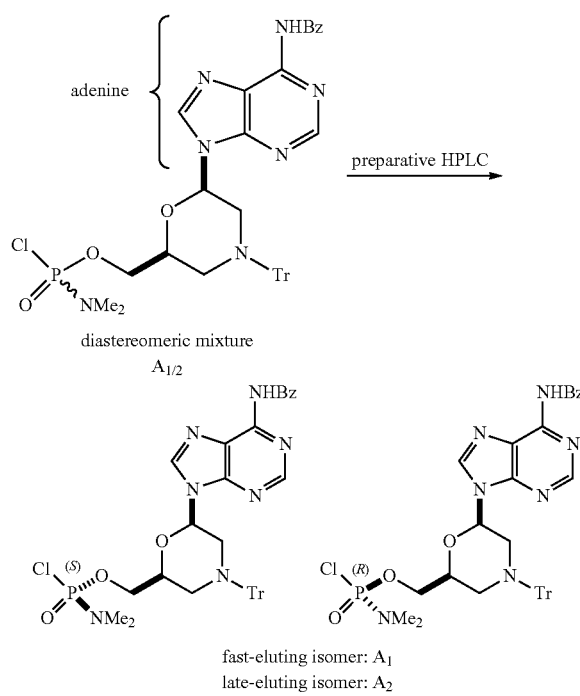

Analytical HPLC Conditions for Activated A Monomers:

| HPLC column | Chiralpak IC, 4.6 × 250 mm, 5u |
| --- | --- |
| Temperature | 35° C. |
| Flow rate | 1 mL/min |
| Mobile phase | Ethyl acetate |
| Gradient | Isocratic |
| Run time | 15 min |
| Injection volume | 10 μL (5 mg/ml, ethyl acetate) |
| Detection | 260 nm |
| Retention Time | A₁  8.1 min |
|  | A₂  11.7 min |

Preparative HPLC Conditions for Activated A Monomers:

Chiralpak IC, 21×250 mm, 5u; Elute with 100% ethyl acetate at 15 ml/minute, room temperature, uv 260 nm detection.

[1H-NMR data for A₁]

¹H NMR (400 MHz, CDCl₃) δ 9.01 (br, 1H), 8.79 (s, 1H), 8.00 (m, 3H), 7.58 (m, 1H), 7.4-7.6 (m, 8H), 7.2-7.4 (m, 10H), 6.42 (d, 1H, J=8.4 Hz), 4.51 (m, 1H), 4.12 (m, 3H), 3.54 (d, 1H, J=12 Hz), 3.25 (d, 1H, J=12 Hz), 2.62 (s, 3H), 2.59 (s, 3H), 1.81 (t, 1H, J=11 Hz), 1.62 (t, 1H, J=11 Hz)

[¹H-NMR data for A₂]

¹H NMR (400 MHz, CDCl₃) δ 9.04 (br, 1H), 8.79 (s, 1H), 8.00 (m, 3H), 7.56 (m, 1H), 7.4-7.6 (m, 8H), 7.2-7.4 (m, 10H), 6.41 (d, 1H, J=8.4 Hz), 4.51 (m, 1H), 4.12 (m, 3H), 3.54 (d, 1H, J=12 Hz), 3.25 (d, 1H, J=12 Hz), 2.64 (s, 3H), 2.61 (s, 3H), 1.82 (t, 1H, J=11 Hz), 1.63 (t, 1H, J=11 Hz)

C. C-Monomers

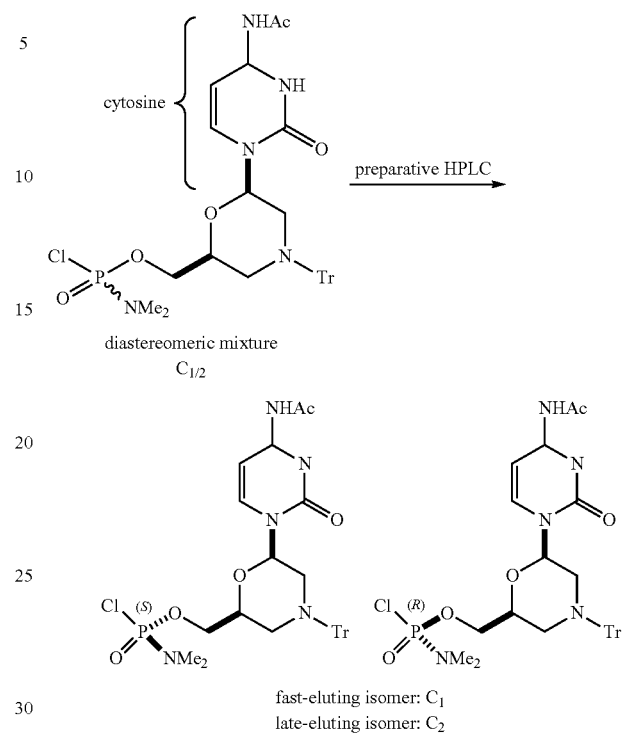

Analytical HPLC Conditions for Activated C Monomers:

| HPLC column | Chiralpak IC, 4.6 × 250 mm, 5u |
| --- | --- |
| Temperature | 35° C. |
| Flow rate | 1.0 mL/min |
| Mobile phase | 90% ethyl acetate 10% n-heptane |
| Gradient | Isocratic |
| Run time | 12 min |
| Injection volume | 10 μL (5 mg/ml, dichloromethane) |
| Detection | 260 nm |
| Retention Time | C₁  6.0 min |
|  | C₂  6.2 min |

Preparative HPLC Conditions for Activated C Monomers:

Chiralpak IC eluted at 15 ml/minute with 75% ethyl acetate and 25% n-heptane. Room temperature and uv 260 nm detection.

[¹H-NMR data for C₁]

¹H NMR (400 MHz, CDCl₃) δ 7.66 (d, 1H, J=7.8 Hz), 7.43 (m, 6H), 7.33 (d, 1H, J=7.4 Hz), 7.15-7.32 (m, 9H), 6.18 (dd, 1H, J=2.2 & 9.2 Hz), 4.42 (m, 1H), 4.08-4.16 (m, 2H), 3.54 (d, 1H, J=11 Hz), 3.14 (d, 1H, J=12 Hz), 2.64 (s, 3H), 2.60 (s, 3H), 2.23 (s, 3H), 1.51 (t, 1H, J=11 Hz), 1.25 (m, 1H).

[¹H-NMR data for C₂]

¹H NMR (400 MHz, CDCl₃) δ 7.64 (d, 1H, J=7.8 Hz), 7.43 (m, 6H), 7.32 (d, 1H, J=7.4 Hz), 7.15-7.32 (m, 9H), 6.19 (dd, 1H, J=2.1 & 9.2 Hz), 4.41 (m, 1H), 4.06-4.15 (m, 2H), 3.54 (d, 1H, J=11 Hz), 3.15 (d, 1H, J=12 Hz), 2.64 (s, 3H), 2.61 (s, 3H), 2.22 (s, 3H), 1.49 (t, 1H, J=11 Hz), 1.25 (m, 1H)

D. G-Monomers (Guanine Mono-Protected)

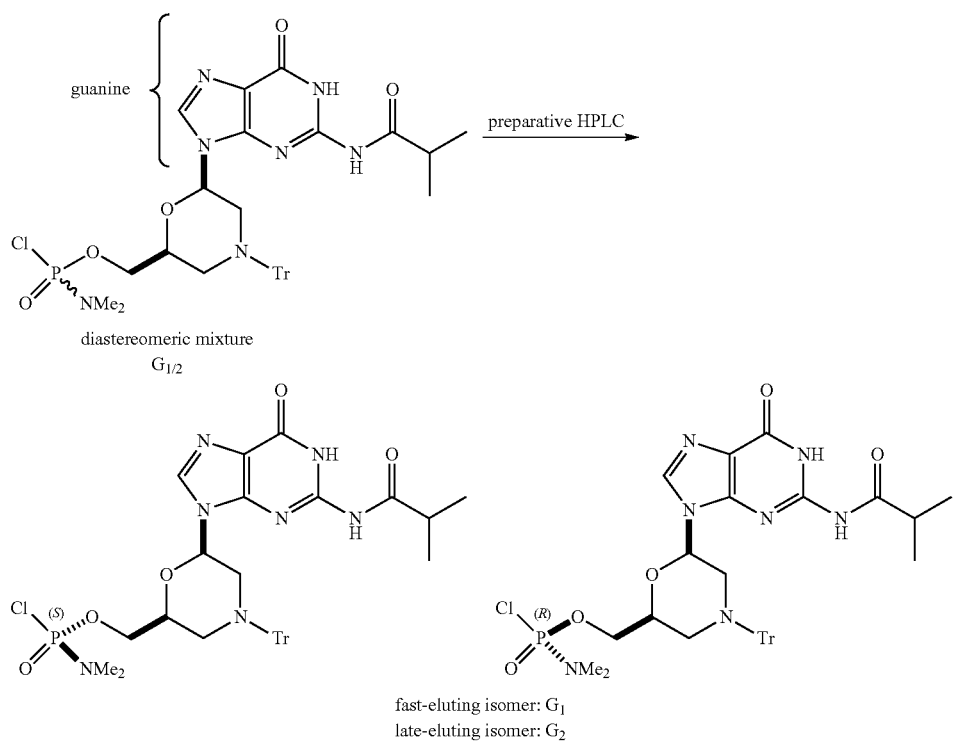

diastereomeric mixture
$G_{1/2}$ fast-eluting isomer: $G_1$
late-eluting isomer: $G_2$ Analytical HPLC Conditions for Activated G Monomers:

| | |
|---|---|
| HPLC column | Chiralpak IC, 4.6 × 250 mm, 5 u |
| Temperature | 35° C. |
| Flow rate | 1.0 mL/min |
| Mobile phase | ethyl acetate |
| Gradient | Isocratic |
| Run time | 30 min |
| Injection volume | 10 μL (5 mg/ml, ethyl acetate) |
| Detection | 260 nm |
| Retention Time | $G_1$ 17.8 min |
| | $G_2$ 22.3 min |

Preparative HPLC Conditions for Activated G Monomers:

Chiralpak IC eluted at 15 ml/minute with 100% ethyl acetate. Room temperature and uv 260 nm detection.

E. T-Monomers

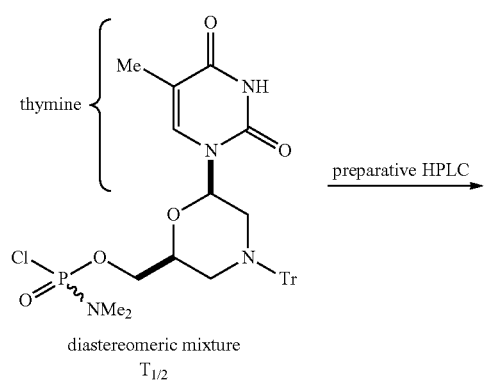

diastereomeric mixture
$T_{1/2}$

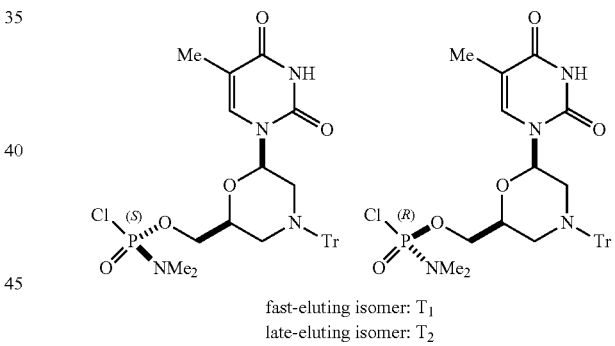

fast-eluting isomer: $T_1$
late-eluting isomer: $T_2$

Analytical HPLC Conditions for Activated T Monomers:

| | |
|---|---|
| HPLC column | Chiralpak IC, 4.6 × 250 mm, 5 u |
| Temperature | 35° C. |
| Flow rate | 1 mL/min |
| Mobile phase | Ethyl acetate |
| Gradient | Isocratic |
| Run time | 10 min |
| Injection volume | 10 μL (5 mg/ml, methylene chloride) |
| Detection | 260 nm |
| Retention Time | $T_1$ 4.5 min |
| | $T_2$ 7.0 min |

Preparative HPLC Conditions for Activated T Monomers:

Chiralpak IC, 50×500 mm, 20u. Elute column at 60 ml/minute with ethyl acetate, room temperature, 260 nm detection. Retention times are 25 and 40 minutes.

[1H-NMR data for T1]

¹H NMR (400 MHz, CDCl₃) δ 7.4-7.5 (m, 5H), 7.26-7.33 (m, 6H), 7.16-7.22 (m, 3H), 7.04 (d, 1H, J=1 Hz), 6.12 (dd, 1H, J=2 & 10 Hz), 4.39 (m, 1H), 4.12 (m, 2H), 3.37 (d, 1H, J=12 Hz), 3.15 (d, 1H, J=12 Hz), 2.66 (s, 3H), 2.63 (s, 3H), 1.83 (d, 1H, J=1 Hz), 1.49 (t, 1H, J=11 Hz), 1.41 (t, 1H, J=11 Hz))

[1H-NMR data for T2]

¹H NMR (400 MHz, CDCl₃) δ 7.4-7.5 (m, 6H), 7.24-7.35 (m, 6H), 7.14-7.22 (m, 3H), 7.03 (s, 1H), 6.12 (dd, 1H, J=2 & 10 Hz), 4.39 (m, 1H), 4.09 (m, 2H), 3.37 (d, 1H, J=11 Hz), 3.15 (d, 1H, J=11 Hz), 2.66 (s, 3H), 2.62 (s, 3H), 1.82 (s, 3H), 1.48 (t, 1H, J=11 Hz), 1.40 (t, 1H, J=11 Hz)

F. C-Monomers (NBz)

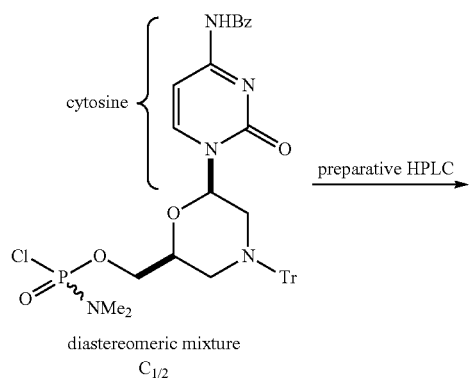

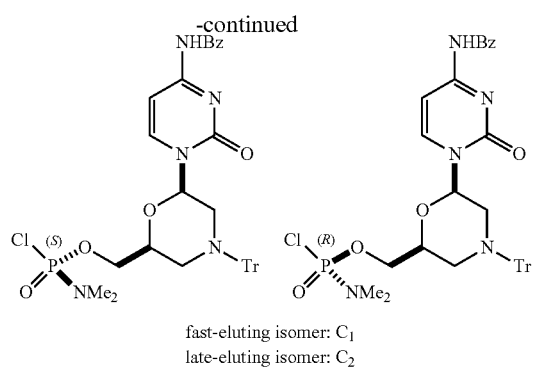

fast-eluting isomer: C₁
late-eluting isomer: C₂

Analytical HPLC Conditions for Activated C Monomers (NBz):

| | | |
|---|---|---|
| HPLC column | Chiralpak IB, 4.6 × 150 mm, 5 u | |
| Temperature | 35° C. | |
| Flow rate | 1.0 mL/min | |
| Mobile phase | 100% acetonitrile | |
| Gradient | Isocratic | |
| Run time | 5 min | |
| Injection volume | 10 μL (5 mg/ml, acetonitrile) | |
| Detection | 260 nm | |
| Retention Time | C₁ | 3.4 min |
| | C₂ | 4.5 min |

Preparative HPLC Conditions for Activated C Monomers (NBz):
Chiralpak IB, 20×250 mm 5u, eluted at 9 ml/minute with 100% acetonitrile. Room temperature and uv 260 nm detection. Retention times are 13 and 16 minutes.

G. G-Monomers (Guanine Doubly Protected)

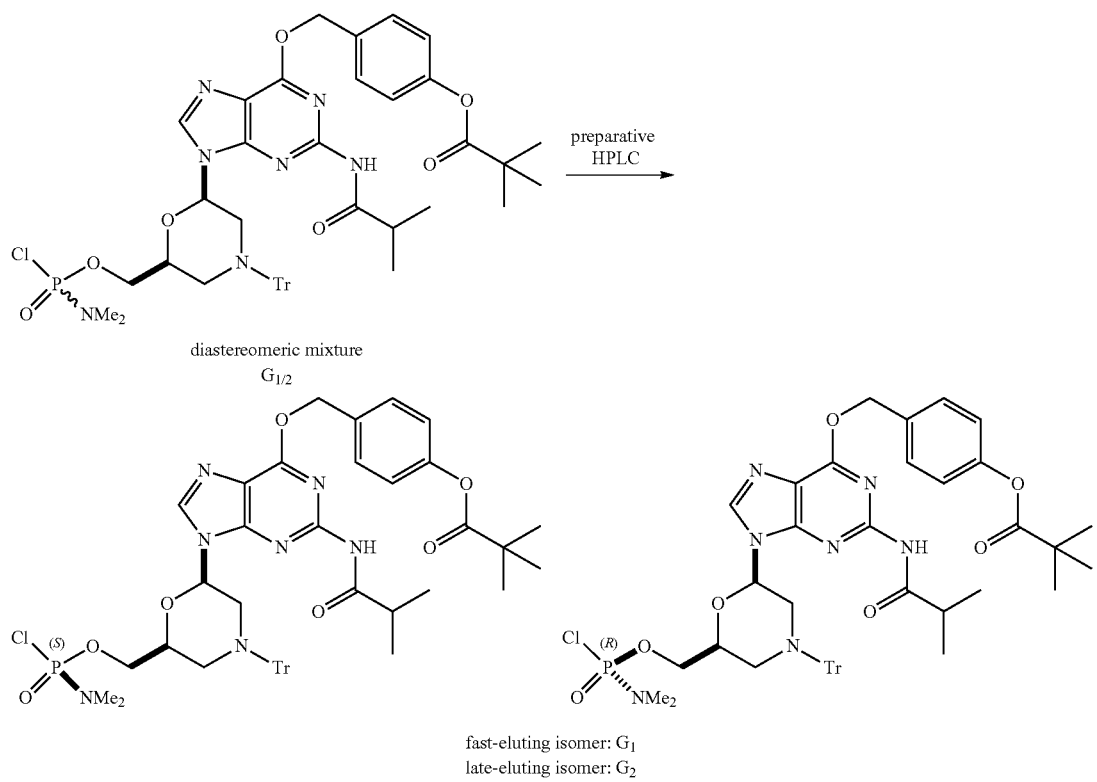

fast-eluting isomer: G₁
late-eluting isomer: G₂

Analytical HPLC Conditions for Activated G Monomers (Guanine Doubly Protected):

| HPLC column | Chiralpak IA, 4.6 × 250 mm, 5 u | |
|---|---|---|
| Temperature | 35° C. | |
| Flow rate | 1.0 mL/min | |
| Mobile phase | 70% ethyl acetate/30% methylene chloride | |
| Gradient | Isocratic | |
| Run time | 8 min | |
| Injection volume | 10 µL (5 mg/ml, ethyl acetate) | |
| Detection | 260 nm | |
| Retention Time | $G_1$ | 3.9 min |
| | $G_2$ | 43 min |

Preparative HPLC Conditions for Activated G Monomers (Guanine Doubly Protected):

Chiralpak IA 50×500 mm, eluted at 60 ml/minute with 100% ethyl acetate. Room temperature and uv 260 nm detection. Retention times are 20 and 24 minutes.

[$^1$H-NMR data for $G_2$ (guanine doubly protected)]
$^1$H NMR (400 MHz, CDCl$_3$) δ 7.78 (s, 1H), 7.77 (s, 1H), 7.50 (d, 2H, J=9 Hz), 7.4-7.5 (m, 6H), 7.26-7.33 (m, 6H), 7.15-7.22 (m, 3H), 7.02 (d, 2H, J=9 Hz), 6.23 (dd, 1H, J=2 & 10 Hz), 5.61 (d, 1H, J=12 Hz), 5.56 (d, 1H, J=12 Hz), 4.47 (m, 1H), 4.1 (m, 2H), 3.47 (d, 1H, J=11 Hz), 3.22 (d, 1H, J=12 Hz), 3.2 (m, 1H), 2.64 (s, 3H), 2.60 (s, 3H), 1.75 (t, 1H, J=11 Hz), 1.58 (t, 1H, J=11 Hz), 1.33 (s, 9H), 1.33 (t, 6H, J=7 Hz)

IV. Examples of Stereospecific PMO Coupling with Diastereomerically Pure Activated Monomers The following examples report use of stereospecific coupling to prepare stereochemically homogeneous products.

A. Activated U-monomers ($U_1$ & $U_2$)+U-Morpholine-NH (1)

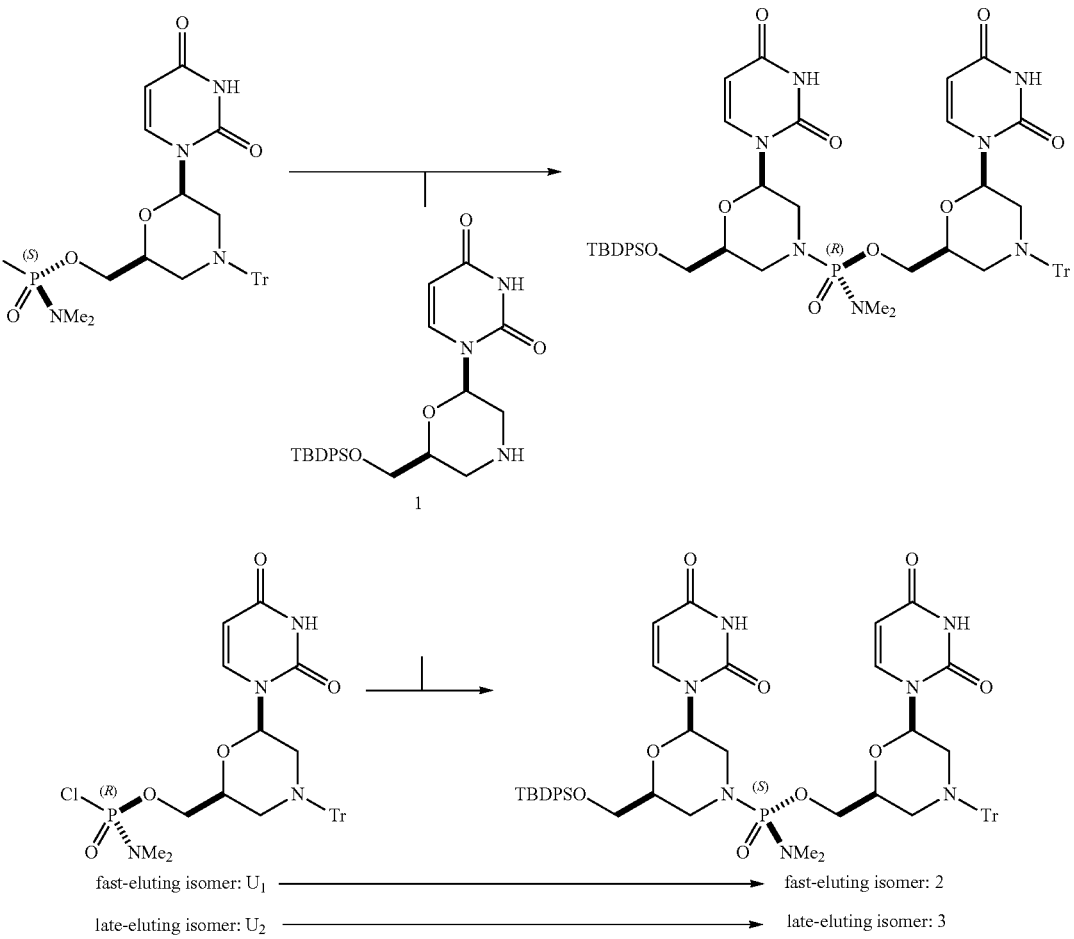

[$^1$H-NMR data for $G_1$ (guanine doubly protected)]
$^1$H NMR (400 MHz, CDCl$_3$) δ 7.76 (s, 2H), 7.50 (d, 2H, J=9 Hz), 7.4-7.5 (m, 6H), 7.26-7.32 (m, 6H), 7.16-7.22 (m, 3H), 7.02 (d, 2H, J=9 Hz), 6.24 (dd, 1H, J=2 & 10 Hz), 5.61 (d, 1H, J=12 Hz), 5.56 (d, 1H, J=12 Hz), 4.48 (m, 1H), 4.1 (m, 2H), 3.47 (d, 1H, J=11 Hz), 3.23 (d, 1H, J=12 Hz), 3.2 (m, 1H), 2.62 (s, 3H), 2.59 (s, 3H), 1.75 (t, 1H, J=11 Hz), 1.57 (t, 1H, J=12 Hz), 1.33 (s, 9H), 1.33 (t, 6H, J=7 Hz)

$U_1$ (11 mg, 0.018 mmol, 1 eq, 99.0% de) was dissolved in acetonitrile (0.11 ml) and mixed with diisopropylethylamine (8 µL, 0.05 mmol, 2.5 eq). U-morpholine-NH (1; 14 mg, 0.030 mmol, 1.6 eq) was added and sonication was applied to aid for dissolution. After 0.5 h stirring, a small aliquot of reaction mixture was diluted with CDCl$_3$ and analyzed by $^1$H NMR. All the rest of reaction mixture was diluted with acetonitrile (8 ml) for HPLC analysis and kept in freezer. Stereospecific formation of 2 was confirmed by HPLC analysis (99.4% de). The above protocol was employed also for the coupling of $U_2$ (95.6% de) to stereospecifically give 3 (96.0% de).

Analytical HPLC Conditions for U/U-Coupling:

| HPLC column | Chiralpak IC, 4.6 × 250 mm, 5 u | |
|---|---|---|
| Temperature | 35° C. | |
| Flow rate | 1.0 mL/min | |
| Mobile phase | 80% methanol 20% acetonitrile | |
| Gradient | Isocratic | |
| Run time | 30 min | |
| Injection volume | 10 μL (2 mg/ml, acetonitrile) | |
| Detection | 260 nm | |
| Retention Time | $U_1$ | 11.5 min |
| | $U_2$ | 21.5 min |
| | 2 | 12.0 min |
| | 3 | 22.1 min |

| nucleophile | activated U monomer | Product (UU dinucleotide) |
|---|---|---|
| U morpholine-NH (1) | $U_1$ (99.0% de) → | 2 (99.4% de) |
| | $U_2$ (95.6% de) → | 3 (96.0% de) |

[$^1$H-NMR data for 2]
$^1$H NMR (400 MHz, CDCl$_3$) δ 7.6 (m, 4H), 7.2-7.5 (m, 20H), 7.1-7.2 (m, 3H), 6.15 (d, 1H, J=8.0 Hz), 5.73 (d, 1H, J=8.0 Hz), 5.66 (d, 1H, J=8.0 Hz), 5.54 (d, 1H, J=8.0 Hz), 4.40 (m, 1H), 3.93 (m, 2H), 3.81 (m, 1H), 3.70 (m, 2H), 3.41 (m, 2H), 3.40 (m, 3H), 3.11 (d, 1H, J=12 Hz), 2.78 (m, 1H), 2.56 (s, 3H; NMe), 2.54 (s, 3H; NMe), 2.48 (m, 1H), 1.47 (t, 1H, J=11 Hz), 1.35 (t, 1H, J=11 Hz), 1.04 (s, 9H)

[$^1$H-NMR data for 3]
$^1$H NMR (400 MHz, CDCl$_3$) δ 7.6 (m, 4H), 7.3-7.5 (m, 11H), 7.2-7.3 (m, 9H), 7.1 (m, 3H), 6.12 (dd, 1H, J=2.0 & 9.6 Hz), 5.71 (d, 1H, J=8.4 Hz), 5.70 (d, 1H, J=8.0 Hz), 5.47 (dd, 1H, J=2.0 & 10.4 Hz), 4.31 (m, 1H), 3.97 (m, 1H), 3.85 (m, 1H), 3.73 (m, 2H), 3.65 (m, 1H), 3.31 (m, 2H), 3.24 (m, 1H), 3.07 (d, 1H, J=12 Hz), 2.68 (m, 1H), 2.65 (s, 3H; NMe), 2.62 (s, 3H; NMe), 2.26 (m, 1H), 1.45 (t, 1H, J=12 Hz), 1.29 (t, 1H, J=11 Hz), 1.04 (s, 9H)

B. Activated C-Monomers ($C_1$ & $C_2$)+C-Morpholine-NH (4)

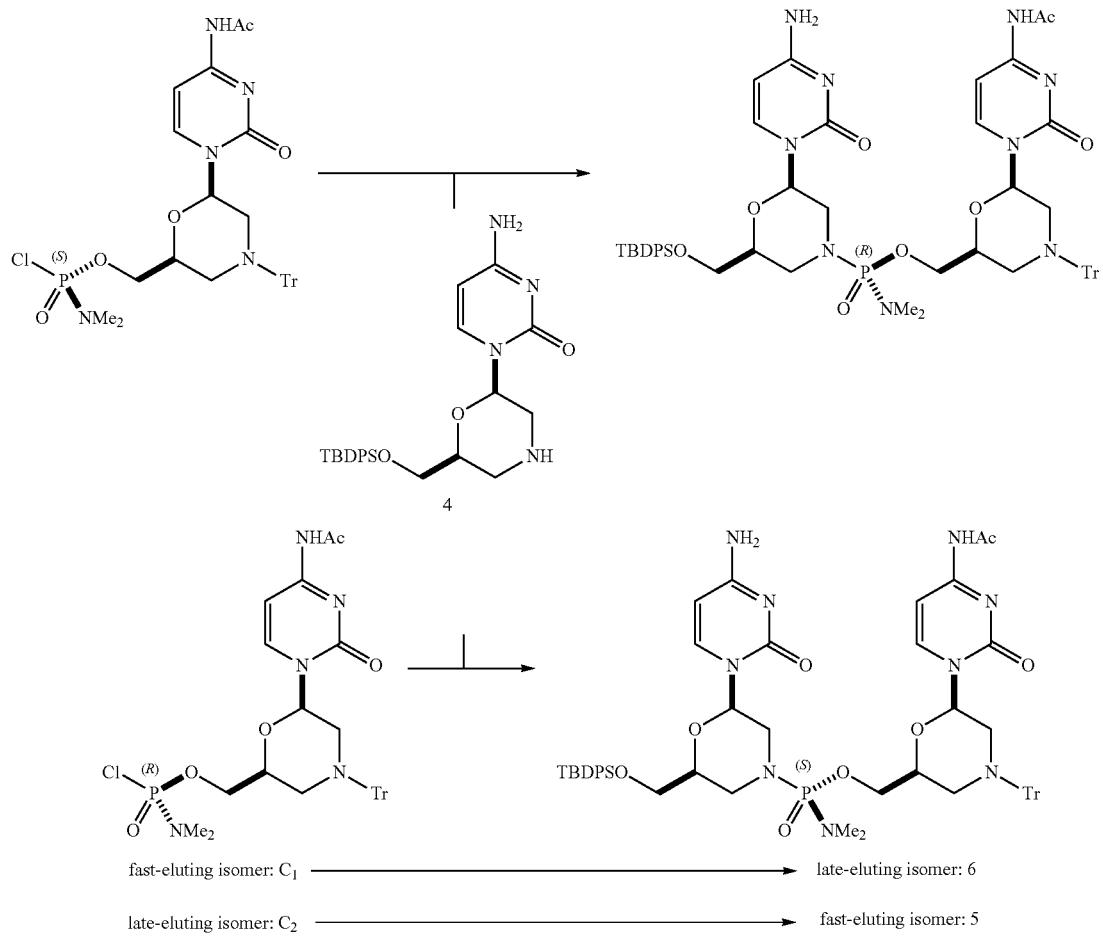

C₁ (20 mg, 0.031 mmol, 1 eq, 93.5% de) was dissolved/ suspended in THF (0.40 ml) and mixed with diisopropylethylamine (12 μL, 0.069 mmol, 2.3 eq). The morpholinocytosine (4; 16 mg, 0.035 mmol, 1.1 eq) dissolved in THF (0.20 mL) was added. After 1.0-2.0 h stirring, a small aliquot of reaction mixture was diluted with acetonitrile and analyzed by LC/MS. An aliquot (30-50 μL) of reaction mixture was diluted with dichloromethane (0.6 ml) for HPLC analysis. Stereospecific formation of 6 was confirmed by HPLC analysis (94.3% de). The reaction mixture was directly loaded onto a silica gel column and eluted with a gradient mobile phase of 0-15% of methanol in ethyl acetate. The above protocol was employed also for the C/C coupling of $C_2$ (90.2% de) to stereospecifically give 5 (90.0% de).

Analytical HPLC Conditions for C/C-Coupling:

| | | |
|---|---|---|
| HPLC column | Chiralpak IC, 4.6 × 250 mm, 5 u | |
| Temperature | 35° C. | |
| Flow rate | 1.0 mL/min | |
| Mobile phase | Solvent A | n-heptane |
| | Solvent B | 1:1 ethanol:methanol 0.1% diethylamine (DEA) |
| Gradient | Isocratic | |
| | % A | % B |
| | 50 | 50 |
| Run time | 20 min | |
| Injection volume | 5 μL (3 mg/ml, dichloromethane) | |
| Detection | 260 nm | |

| | | | |
|---|---|---|---|
| Retention Time | 4 | | 5.4 min |
| | 5 | | 10.5 min |
| | 6 | | 12.9 min |
| nucleophile | activated C monomer | | Product (CC dinucleotide) |
| C morpholine-NH (4) | $C_1$ (93.5% de) | → | 6 (94.3% de) |
| | $C_2$ (90.2% de) | → | 5 (90.0% de) |

[¹H-NMR data for 5]
¹H NMR (400 MHz, CDCl₃) δ 10.9 (br, 1H), 7.69 (d, 1H, J=7.4 Hz), 7.62 (m, 5H), 7.35-7.44 (m, 13H), 7.21-7.35 (m, 6H), 7.15 (m, 4H), 6.14 (br d, 1H, J=7.8 Hz), 5.58 (dd, 1H, J=2.4 & 9.4 Hz), 5.53 (br, 1H), 4.51 (dd, 1H, J=8.6 & 10 Hz), 4.09 (m, 1H), 3.70-3.80 (m, 4H), 3.60 (dd, 1H, J=6.3 & 10 Hz), 3.56 (d, 1H, J=11 Hz), 3.28 (m, 1H), 2.96 (d, 1H, J=11 Hz), 2.69 (s, 3H; NMe), 2.67 (s, 3H; NMe), 2.65 (m, 1H), 2.25 (m, 1H), 2.07 (s, 3H), 1.31 (t, 1H, J=11 Hz), 1.13 (t, 1H, J=11 Hz), 1.04 (s, 9H).

[¹H-NMR data for 6]
¹H NMR (400 MHz, CDCl₃) δ 9.57 (br, 1H), 7.62-7.70 (m, 7H), 7.35-7.50 (m, 14H), 7.23-7.35 (m, 4H), 7.12 (m, 4H), 6.31 (m, 1H), 5.79 (m, 1H), 5.70 (m, 1H), 4.61 (m, 1H), 4.03 (m, 1H), 3.80-3.90 (m, 2H), 3.72 (m, 2H), 3.58 (m, 1H), 3.48 (m, 1H), 3.09 (m, 1H), 2.75 (m, 1H), 2.58 (s, 3H; NMe), 2.55 (s, 3H; NMe), 2.53 (m, 1H), 2.38 (m, 1H), 2.21 (s, 3H), 1.47 (t, 1H, J=10 Hz), 1.22 (t, 1H, J=10 Hz), 1.06 (s, 9H).

C. Activated A-Monomers ($A_1$ & $A_2$)+U-Morpholine-NH (1)

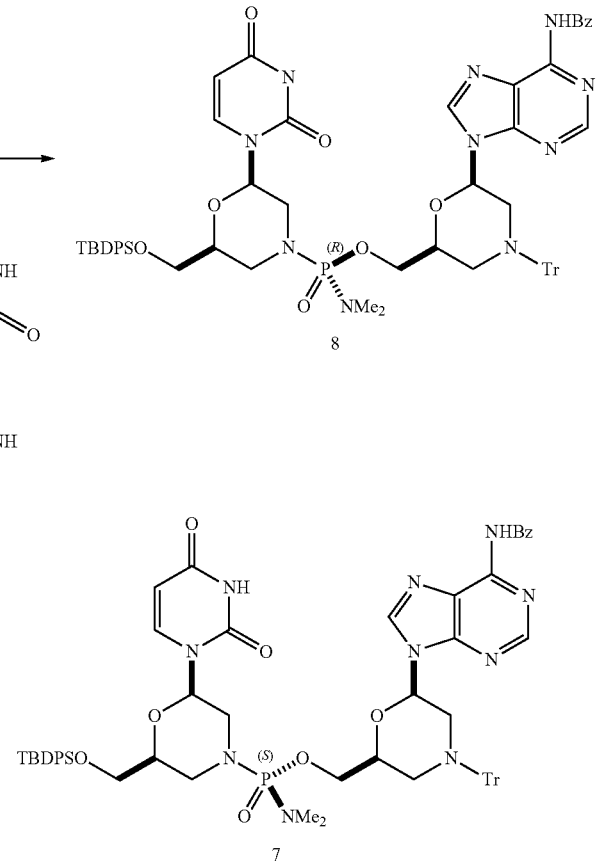

fast-eluting isomer: A₁ - (S) ⟶ late-eluting isomer: 8 - (R)

late-eluting isomer: A₂ - (R) ⟶ fast-eluting isomer: 7 - (S)

A₁ (5.9 mg, 0.008 mmol) was suspended in acetonitrile (118 μL). Diisopropylethylamine (5 μL, 0.03 mmol) was added followed by morpholino-uracil (1; 4.6 mg, 0.01 mmol). Sonication was applied for 1 min and resultant homogeneous mixture was stirred at ambient temperature. After overnight stirring, the mixture (thick white paste) was diluted with a mixture of acetonitrile (5.0 ml) and methanol (0.30 ml) to give homogeneous clear solution. A small aliquot was directly analyzed by HPLC without further dilution.

A₂ (F2; 5.0 mg, 0.007 mmol) was suspended in acetonitrile (100 μl). Diisopropylethylamine (4 μl, 0.02 mmol) was added followed by morpholino-uracil (4.1 mg, 0.009 mmol). Sonication was applied for 1 min and resultant thick suspension was stirred at ambient temperature. After overnight stirring, acetonitrile (5.0 ml) was added and sonication was applied to give homogeneous clear solution. A small aliquot was directly analyzed by HPLC without further dilution.

Analytical HPLC Conditions for U/A-Coupling:

| | | |
|---|---|---|
| HPLC column | Chiraipak IC, 4.6 × 250 mm, 5 u | |
| Temperature | 35° C. | |
| Flow rate | 1 mL/min | |
| Mobile phase | Solvent A | Ethyl acetate |
| | Solvent B | 1:1 ethanol/methanol with 0.1% diethylamine |
| Gradient | Isocratic: 98% solvent A, 2% solvent B | |
| Run time | 30 min | |
| Injection volume | 5 μL (1 mg/ml, acetonitrile-methanol) | |
| Detection | 260 nm | |
| Retention Time | 7 (S isomer) | 21.7 min |
| | 8 (R isomer) | 24.9 min |

| nucleophile | activated A monomer | | Product (UA dinucleotide) |
|---|---|---|---|
| U morpholine-NH (1) | A₁ (97.8% de) | → | 8 (R isomer, 96.2% de) |
| | A₂ (98.4% de) | → | 7 (S isomer 98.3% de) |

D. Activated G-Monomers (G₁ & G₂)+U-Morpholine-NH (1)

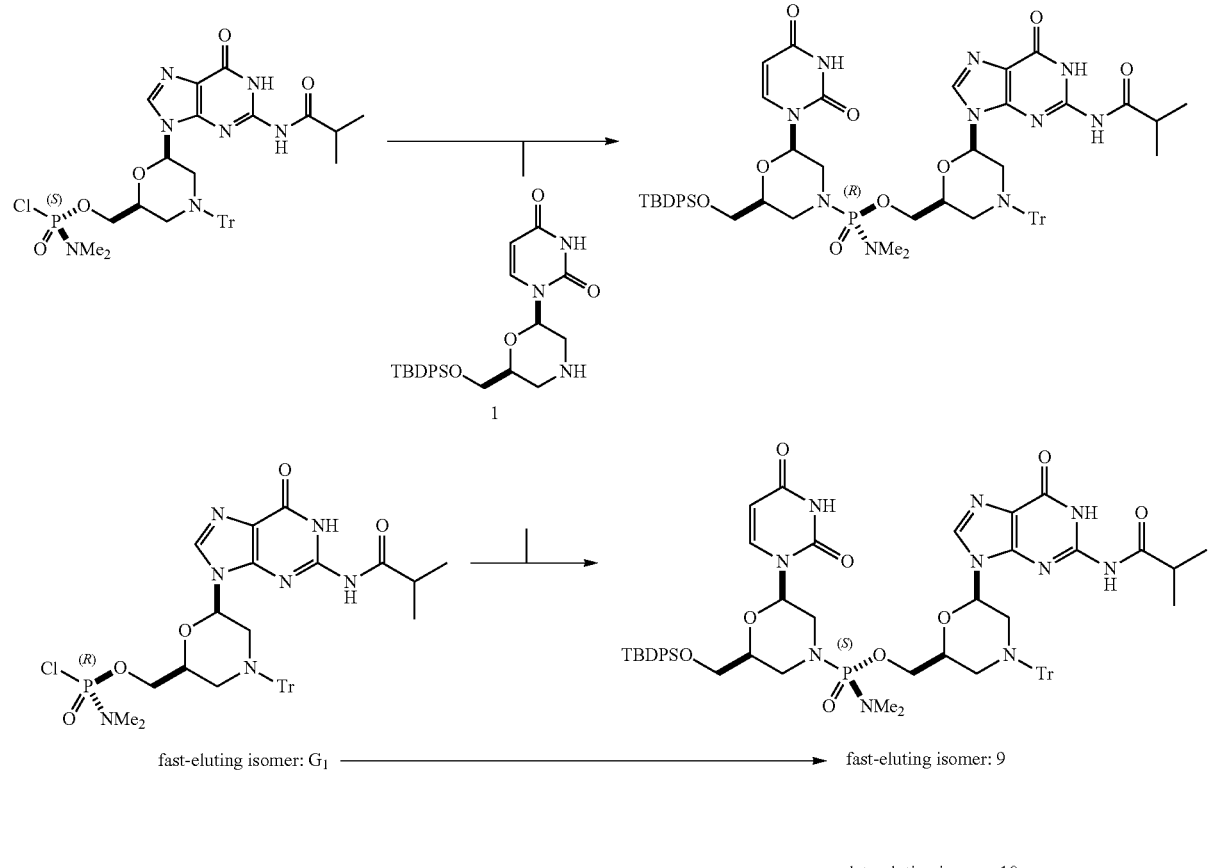

fast-eluting isomer: G₁ ⟶ fast-eluting isomer: 9 late-eluting isomer: G₂ ⟶ late-eluting isomer: 10

G₁ (6.5 mg, 0.009 mmol, 1 eq, 99.9% de) was dissolved/suspended in THF (0.13 ml) and mixed with diisopropylethylamine (3.6 μL, 0.02 mmol, 2.2 eq). The morpholinouracil (1; 4.7 mg, 0.010 mmol, 1.1 eq) dissolved in THF (0.07 mL) was added. After 1.0-2.0 h stirring, a small aliquot of reaction mixture was diluted with acetonitrile and analyzed by LC/MS. An aliquot (100 μL) of reaction mixture was diluted with dichloromethane (0.4 ml) for HPLC analysis. Stereospecific formation of 9 was confirmed by HPLC analysis (99.9% de).

Analytical HPLC Conditions for U/G-Coupling:

| HPLC column | Chiralpak IA, 4.6 × 250 mm, 5 u | | |
|---|---|---|---|
| Temperature | 35° C. | | |
| Flow rate | 1.0 mL/min | | |
| Mobile phase | Solvent A | n-heptane | |
| | Solvent B | Ethyl acetate | |
| | Solvent C | 1:1 ethanol:methanol 0.1% diethylamine (DEA) | |
| Gradient | Isocratic | | |
| | % A | % B | % C |
| | 55 | 40 | 5 |
| Run time | 30 min | | |
| Injection volume | 5 μL (2 mg/ml, dichloromethane) | | |
| Detection | 260 nm | | |
| Retention Time | 1 | 8.4 min | |
| | 9 | 14.0 min | |
| | 10 | 16.3 min | |

| nucleophile | activated G monomer | | Product (UG dinucleotide) |
|---|---|---|---|
| U morpholine-NH (1) | G₁ (99.9% de) | → | 9 (99.9% de) |

Diastereomerically substantially pure compounds as reported above may be used to prepare stereochemically pure oligonucleotides and other compounds. Examples of potential oligonucleotides are shown, for example, in Summerton, J (1999). "Morpholino Antisense Oligomers: The Case for an RNase-H Independent Structural Type.". Biochimica et Biophysica Acta 1489 (1): 141-58; and in Summerton, J; Weller D. (1997). "Morpholino Antisense Oligomers: Design, Preparation and Properties". Antisense & Nucleic Acid Drug Development 7 (3): 187-95. Both of those documents are incorporated by reference herein.

V. Example of Stereospecific Synthesis of 16-Mer PMOs and Differentiation of Stereoisomers by Biophysical Assay This example reports a synthesis that targets a pair of stereopure 16-mer PMOs through stereospecific coupling using activated monomers. These PMOs have opposite stereochemical arrays for their phosphorous linkages.

Target Sequence:

Stereopure Active Monomers (Building Blocks):

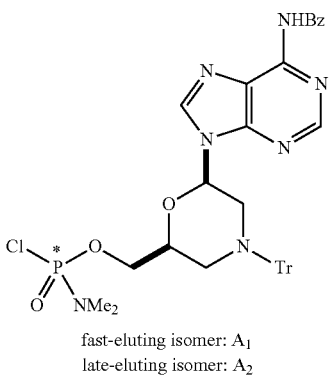

fast-eluting isomer: A₁
late-eluting isomer: A₂

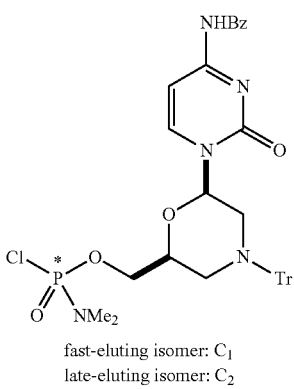

fast-eluting isomer: C₁
late-eluting isomer: C₂

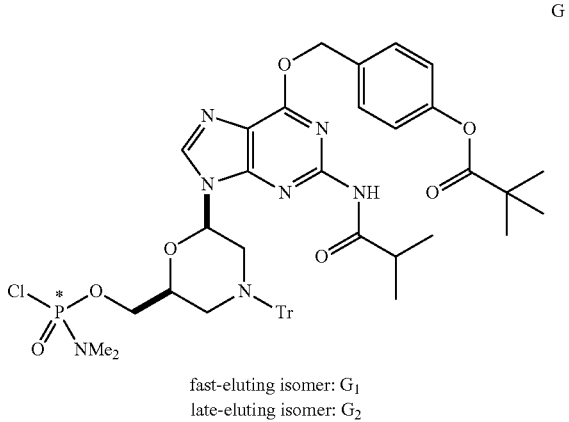

fast-eluting isomer: G₁
late-eluting isomer: G₂

(SEQ ID NO: 2)

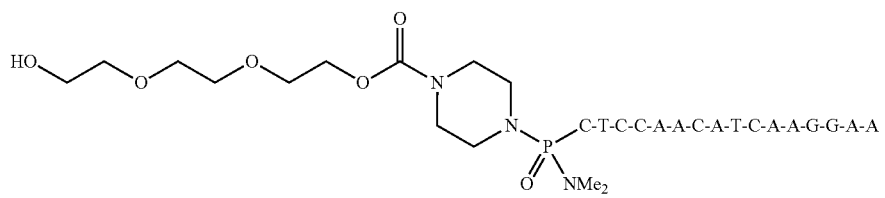

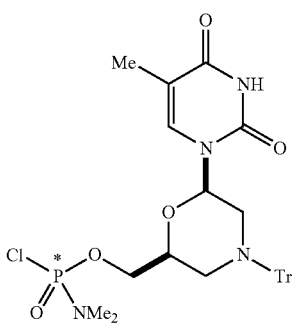

fast-eluting isomer: T₁
late-eluting isomer: T₂

| Target PMOs | Stereopure active monomers used for coupling |
|---|---|
| Stereoisomer 1 | A$_2$, C$_2$, G$_1$ and T$_1$ |
| Stereoisomer 2 | A$_1$, C$_1$, G$_2$ and T$_2$ |

Figure 6:
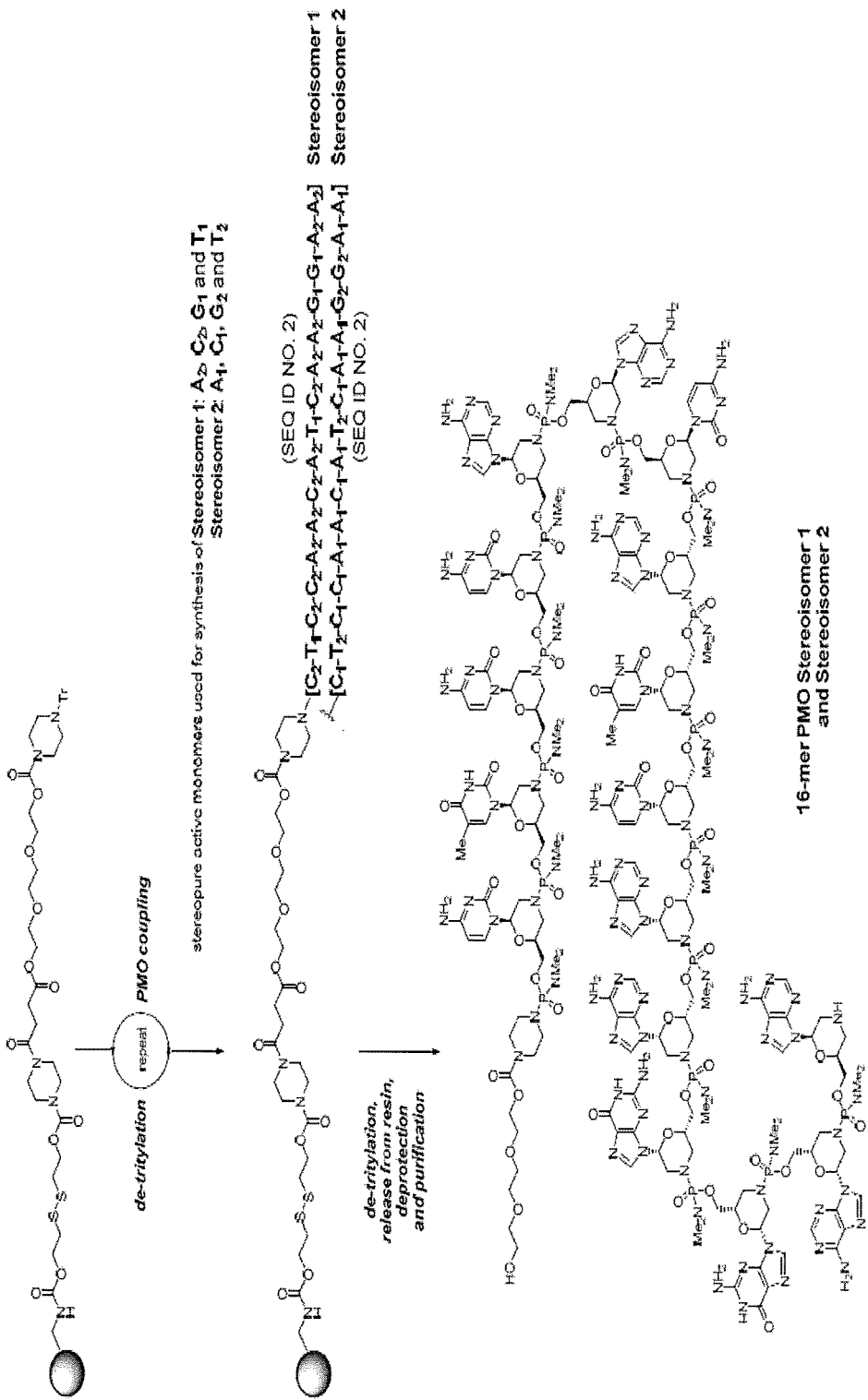
FIG. 6 shows a scheme for stereospecific synthesis of 16-mer PMOs and differentiation of stereoisomers by biophysical assay.

A scheme for stereospecific synthesis of 16-mer PMOs and differentiation of stereoisomers by biophysical assay is shown in FIG. 6. The 16-mer PMO stereoisomers 1 and stereoisomer 2 were prepared manually by solid-phase synthesis on aminomethylpolystyrene-disulfide resin (~300 µmol/g loading, see U.S. Patent App. Pub. No. 20090131624A1, which is incorporated by reference herein) at 50 mg scale (starting resin weight).

Stock Solutions for Solid-Phase Synthesis:

| | |
|---|---|
| De-tritylation | 4-cyanopyridine trifluoroacetate (CYTFA) 2% (w/v) and 0.9% ethanol (v/v) in 20% trifluoroethanol/DCM (v/v). |
| Neutralization | 5% diisopropylethylamine (v/v) in 25% isopropanol/DCM (v/v). |
| Coupling | Freshly prepared 55 mM solution in NEM-DMI* for each of stereopure active monomers (A$_2$, C$_2$, G$_1$ and T$_1$ for stereoisomer 1; A$_1$, C$_1$, G$_2$ and T$_2$ for stereoisomer 2) |

*0.11M N-ethylmorpholine in 1,3-dimethylimidazolidinone (DMI)

Operational Cycle for Each PMO Coupling:

| Step | Volume (ml) | Time (min) |
|---|---|---|
| DCM | 1-2 | 2-5 |
| Detritylation | 1-2 | 5 |
| Detritylation | 1-2 | 5 |
| Detritylation | 1-2 | 5 |
| Detritylation | 1-2 | 5 |
| Detritylation | 1-2 | 5 |
| DCM | 1-2 | 2-5 |
| Neutralization | 1-2 | 2-5 |
| Neutralization | 1-2 | 2-5 |
| Neutralization | 1-2 | 2-5 |
| Neutralization | 1-2 | 2-5 |
| DCM | 1-2 | 2-5 |
| DCM | 1-2 | 2-5 |
| DCM | 1-2 | 2-5 |
| Coupling | 1 | >180* |
| DCM | 1-2 | 2-5 |
| Neutralization | 1-2 | 2-5 |
| Neutralization | 1-2 | 2-5 |
| DCM | 1-2 | 2-5 |
| DCM | 1-2 | 2-5 |
| DCM | 1-2 | 2-5 |
| DCM | 1-2 | 2-5 |

*40° C. for 3 hours or room temperature for 12 hours.

Release from Resin and Deprotection:

To the resin-bound 16-mer (after de-tritylation) was added 1:3 (v/v) of 28% aqueous ammonia/ethanol (~5 ml). The mixture was sealed and heated at 45° C. for 20 hours. After cooling to room temperature, the mixture was filtered and washed with methanol. The filtrate was concentrated and diafiltered against 15 mM triethylammonium (TEAA) buffer pH 7.0. The apparatus used was an Amicon Stirred Cell (50 mL) with an Ultracel 1 kDa UF membrane. The samples were diafiltered by dilution/concentration until the original solvent was reduced to 1% original concentration (approximately 5 cycles) and then subjected to reverse phase preparative HPLC purification.

Reverse Phase Preparative HPLC Method for PMO Purification:

| | | | |
|---|---|---|---|
| HPLC column | XBridge Prep C8 OBD column, 9 × 150 mm, 5 µm | | |
| Column temperature | ambient temperature | | |
| Flow rate | 30.0 ml/min | | |
| Gradient | Time (min) | % A | % B |
| | Initial | 85 | 15 |
| | 18 | 80 | 20 |
| | 20 | 0 | 100 |
| Mobile phase | Solvent A: 15 mM Triethylammonium acetate (TEAA) buffer pH 7 + 10% MeOH | | |
| | Solvent B: acetonitrile + 10% MeOH | | |
| Diluting solution | 15 mM TEAA buffer | | |
| Run time | 20 min | | |
| Detection | UV 260 nm | | |
| Retention time | Stereoisomer 1 | 13.98 min | |
| | Stereoisomer 2 | 14.03 min | |

LC/MS Method for Quality Assessment of PMOs:

| | | | |
|---|---|---|---|
| HPLC column | Waters BEH C18 Oligo 2.1 × 50 mm 130 Angstrom 1.7 um | | |
| Column temperature | 45° C. | | |
| Flow rate | 0.3 mL/min | | |
| Gradient | Time (min) | % A | % B |
| | Initial | 95 | 5 |
| | 2 | 95 | 5 |
| | 20 | 50 | 50 |
| | 24 | 50 | 50 |
| | 24.1 | 95 | 5 |
| | 30 | 95 | 5 |
| Mobile phase | Solvent A: 50 mM Ammonium acetate | | |
| | Solvent B: Acetonitrile/Methanol 1/1 v/v with 50 mM Ammonium acetate | | |
| Run time | 30 min | | |
| Injection volume | 25 µL Diluent: water or 10 mM Triethylamine acetate | | |

-continued

| | | |
|---|---|---|
| Detection | UV 260 nm | |
| MS/Ionization mode | Synapt G2/Electrospray Positive Mode | |
| Cone voltage/Extraction | 30 V/4 V/2.8 kV | |
| Source Temp./ Collision energies/ MS function/Analysis | 100° C./4 eV (low energy) 40-70 eV (high energy/$MS^E$ mode/Deconvolution and Deisotoping using Waters MSe Viewer Software | |
| Retention time | Stereoisomer 1 | 10.83 min |
| | Stereoisomer 2 | 10.86 min |

Materials and Conditions for Melting Temperature (Tm) Measurement

| | |
|---|---|
| complimentary RNA (16-mer) | 5'-UUCCUUGAUGUUGGAG-3' (SEQ ID NO. 1) (IDT Integrated DNA Technologies) |
| Diluting buffer | 10 mM Sodium Phosphate, 100 mM NaCl, 0.1 mM EDTA, pH 7.0 (adjusted with phosphoric acid) |
| Thermal Melt Apparatus | Shimadzu 2700 UV-Vis Spectrophotometer equipped with the Shimadzu S-1700 Temperature Module |
| Vacuum Centrifugation Concentrator | Labconco Centrivap Concentrator Model 7810015 |
| Stock solutions | 8 µM in 250 µL buffer of each sample and complimentary RNA were prepared using the Dilution buffer from samples concentrated and dried by vacuum centrifugation |
| Procedure | Each sample was then mixed with an equivalent volume of 8 µM complimentary RNA The mixtures were heated to 95° C. and then cooled to 25° C. for annealment prior to the Tm measurement. Tm analysis (UV 260 nm) was conducted from 25° C. to 105° C. at 0.5° C./min (with the temperature returning to starting conditions after each run) and then repeated under the same conditions. Tm Analysis software (Shimadzu) was used to calculate the Tm using the "averaging" function. |

Summary for Thermal Melt Characterization of Complexes of Stereochemically Distinct PMOs with Complimentary RNAs:

| | LC/MS purity (area %) | Tm (° C.) |
|---|---|---|
| Stereoisomer 1 | 97.6 | 62.8 |
| Stereoisomer 2 | 94.2 | 57.2 |

Figure 7:
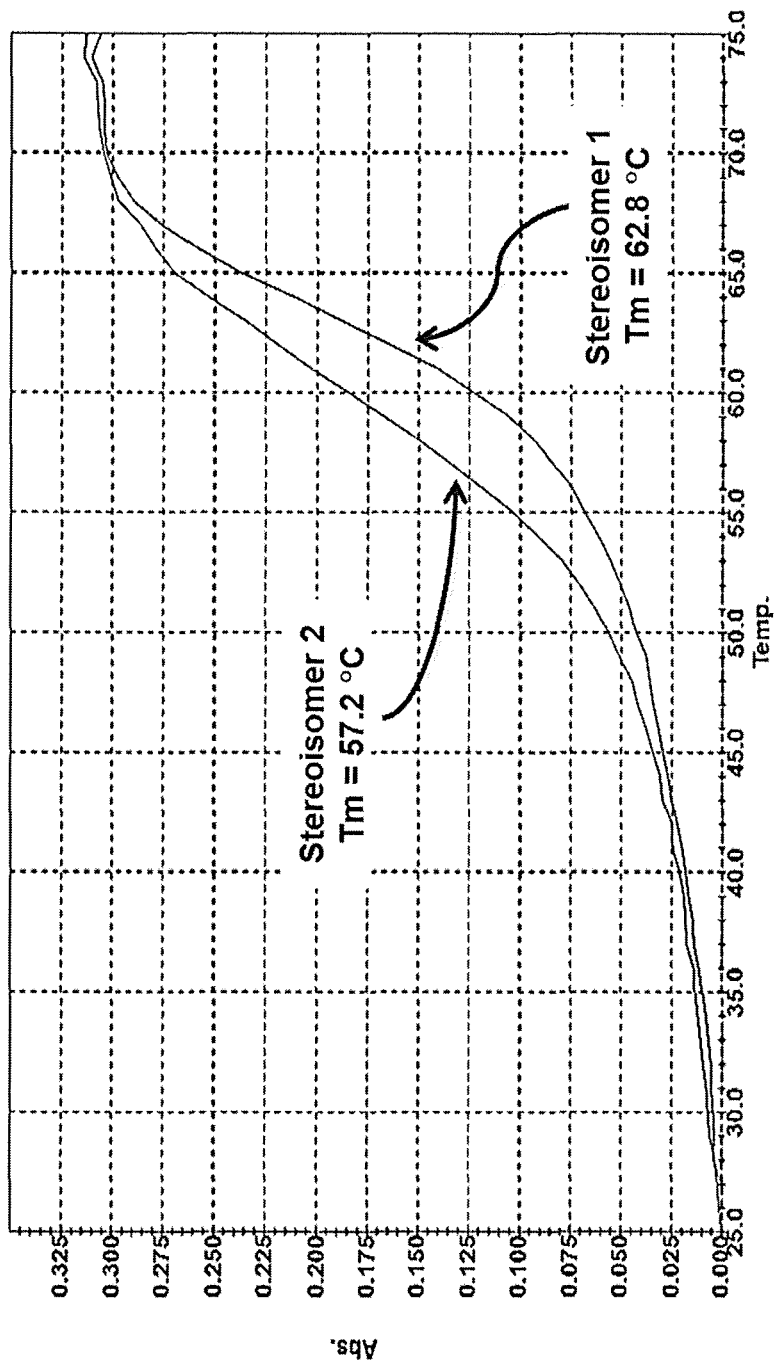
FIG. 7 shows melting points for Stereoisomers 1 and 2 of the example showing stereospecific synthesis of 16-mer PMOs and differentiation of stereoisomers by biophysical assay, as reported below.

Melting points for Stereoisomers 1 and 2 are shown in FIG. 7. Based on the different melting points, one may conclude that separate amounts of substantially pure stereoisomers have been prepared.

VI. Example of Stereospecific Synthesis and Absolute Stereochemical Assignment of Stereopure PMO Dinucleotide Compound 100 (5'-TA$_2$-3')

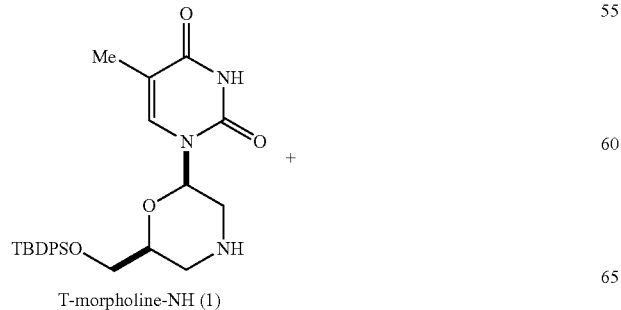

T-morpholine-NH (1)

-continued

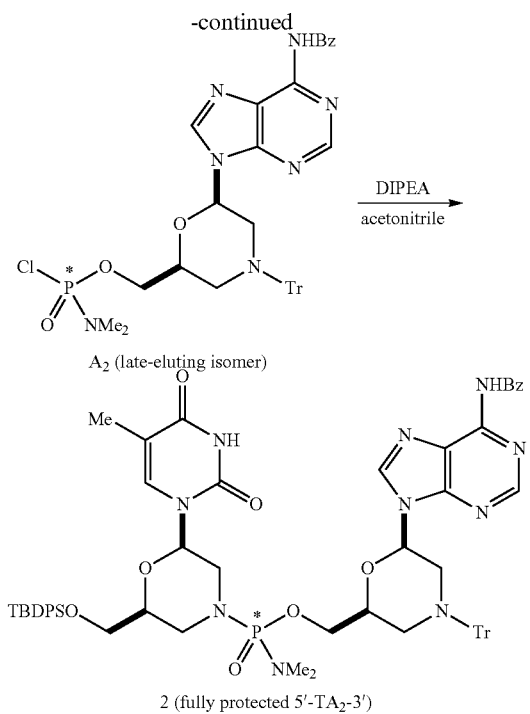

A$_2$ (late-eluting isomer)

2 (fully protected 5'-TA$_2$-3')

Late-eluting active A monomer (A$_2$; 200 mg, 0.277 mmol, 1 eq) was dissolved in a mixture of acetonitrile (2.0 ml) and DIPEA (0.12 ml, 0.69 mmol, 2.5 eq). T-morpholine-NH (1; 146 mg, 0.305 mmol, 1.1 eq) was then added and resultant suspension was sonicated for a few minutes until a clear solution was obtained. The reaction mixture was stirred at room temperature overnight. Upon complete reaction monitored by LC/MS, the mixture was concentrated and subjected to column chromatography (3% methanol in DCM, Biotage SnapUltra 10 g SiO$_2$). Clean product fractions were combined and concentrated under vacuum to give the fully protected stereopure 5'-TA-3' dinucleotide 2 as a white solid (240 mg, 0.206 mmol, 74% yield).

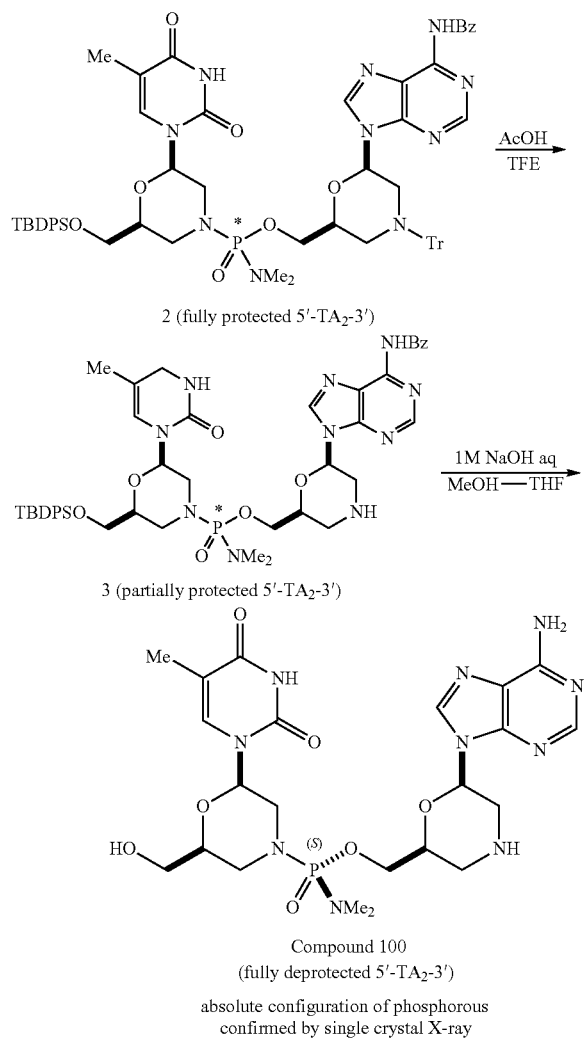

2 (fully protected 5'-TA$_2$-3')

3 (partially protected 5'-TA$_2$-3')

Compound 100
(fully deprotected 5'-TA$_2$-3')

absolute configuration of phosphorous
confirmed by single crystal X-ray

To the fully protected dinucleotide 2 (500 mg, 0.429 mmol) in 25 ml flask was added 2,2,2-trifluoroethanol (TFE; 4.0 ml) and acetic acid (1.0 ml) at room temperature. The resultant mixture was stirred at room temperature and monitored by LC/MS. After 30 minutes, the reaction was quenched with saturated aqueous NaHCO$_3$ and DCM. The two layers were separated and the aqueous layer was back extracted. All organic layers were combined, washed with half-saturated brine, dried over anhydrous Na$_2$SO$_4$, filtered and concentrated to give crude product as white foam. The crude product was purified by column chromatography (20% MeOH in acetone, Biotage Snap Ultra 25 g SiO$_2$ cartridge) to give the partially protected dinucleotide 3 as a glassy solid (300 mg, 0.325 mmol, 76% yield).

The partially protected dinucleotide 3 (250 mg, 0.271 mmol) was dissolved in a mixture of methanol (12.5 ml) and THF (12.5 mL) and treated with 1 M NaOH (10.8 ml) at room temperature. After stirring at room temperature for 22 h (progress monitored by LC/MS), the mixture was neutralized with 1 M HCl (10.8 mL) to adjust pH at 8 and then concentrated under vacuum to dryness. The residue was dissolved in water (5 mL) and washed with EtOAc (5 mL). The aqueous layer was concentrated under vacuum to dryness to give crude product as white solid (480 mg). The crude product was purified by size-exclusion chromatography (Sephadex® LH-20, MeOH/water 4:1) to give the fully deprotected dinucleotide Compound 100 as white solid (137 mg, 0.236 mmol, 87% yield).

Figure 8:
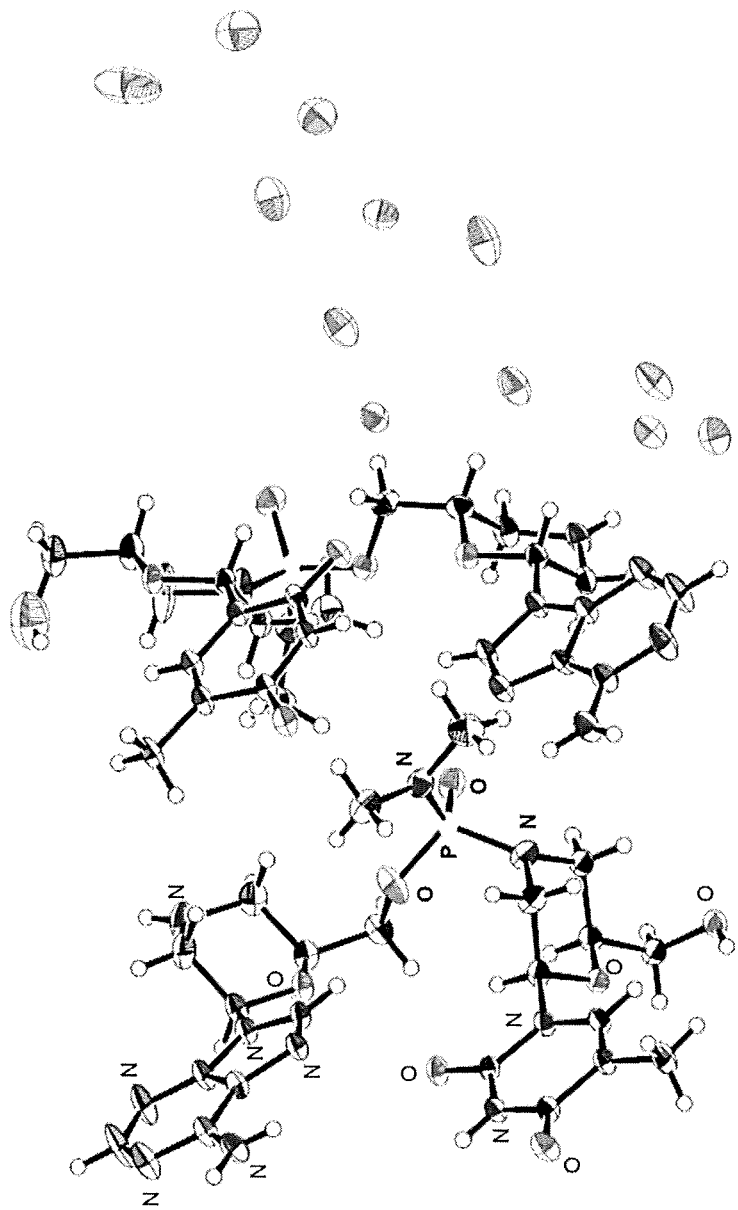
FIG. 8 shows an ORTEP plot of crystalline Compound 100, as reported below.
Figure 9B:
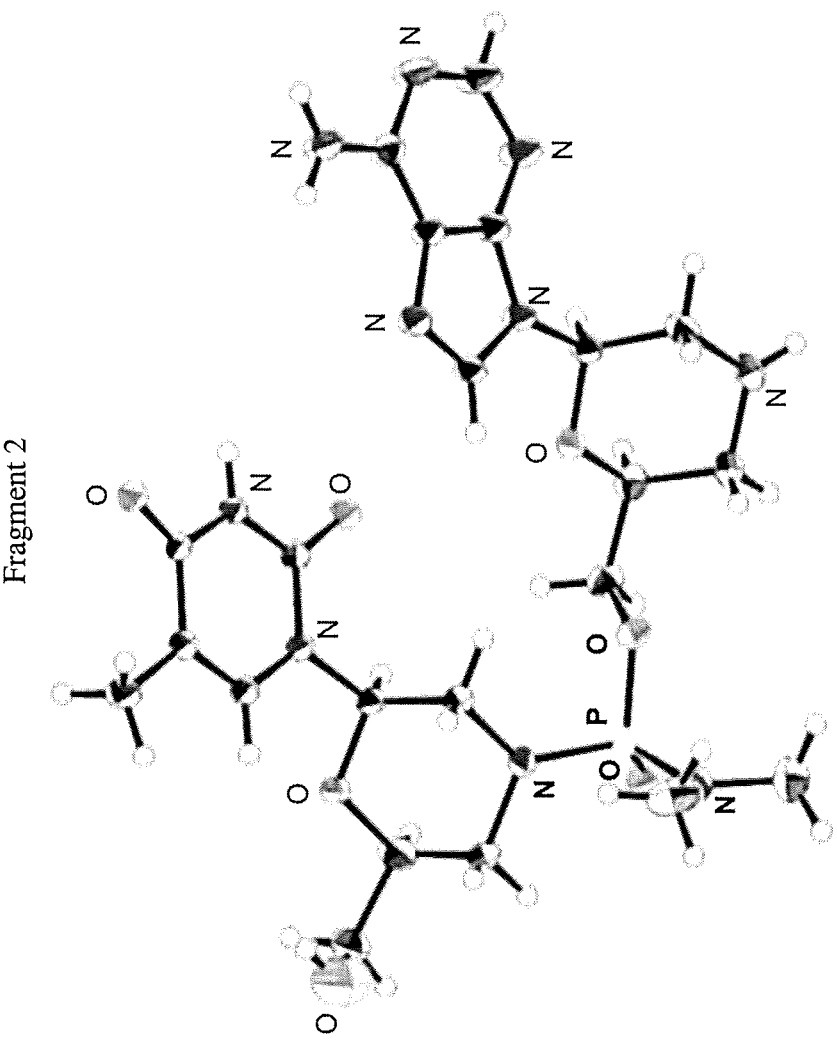

A drop of Compound 100 aqueous solution (200 mg/ml) was sealed in a well with pure water for one day to grow single crystals. X-ray structure of the single crystal confirmed absolute configuration of the phosphorous linkage as S. This X-ray structure is shown in an ORTEP plot in FIG. 8. ORTEP plots of separate fragments are shown in FIG. 9A and FIG. 9B. X-ray data was collected as reported below.

Data Collection

A single crystal of Compound 100 ($C_{22}H_{33}N_{10}O_7P$) was mounted on a glass fiber. All measurements were made on a diffractometer using graphite monochromated Cu-Kα radiation.

Cell constants and an orientation matrix for data collection, obtained from a least-squares refinement using the setting angles of 36473 carefully centered reflections in the range 7.75<2θ<147.10° corresponded to a C-centered monoclinic cell with dimensions:

a=33.3523(2) Å
b=13.80020(11)Å  β=96.8075(6)°
c=14.19956(10) Å
V=6489.53(8) Å$^3$

For Z=4 and F.W.=580.54, the calculated density is 0.594 g/cm$^3$. Based on the reflection conditions of:

*hkl*: h+k=2n packing considerations, a statistical analysis of intensity distribution, and the successful solution and refinement of the structure, the space group was determined to be:

C2 (#5)

The data were collected at a temperature of 23±10° C. using the ω-2θ scan technique to a maximum 2θ value of 147.7°. Omega scans of several intense reflections, made prior to data collection, had an average width at half-height of 0.00° with a take-off angle of 6.0°. Scans of (0.00+0.00 tan θ)° were made at a speed of 0.0°/min (in ω).

Data Reduction 50795 reflections were collected, where 12008 were unique (Rint=0.0453). Data were collected and processed using CrysAlisPro (Rigaku Oxford Diffraction). (CrysAlisPro: Data Collection and Processing Software, Rigaku Corporation (2015). Tokyo 196-8666, Japan). No decay correction was applied.

The linear absorption coefficient, μ, for Cu-Kα radiation is 6.011 cm$^{-1}$. An empirical absorption correction was applied that resulted in transmission factors ranging from 0.341 to 1.000. The data were corrected for Lorentz and polarization effects.

Structure Solution and Refinement

The structure was solved by direct methods (SHELXT Version 2014/5: Sheldrick, G. M. (2014). *Acta Cryst. A*70, C1437) and expanded using Fourier techniques. The non-hydrogen atoms were refined anisotropically. Hydrogen atoms were refined using the riding model. The final cycle of full-matrix least-squares refinement (using Least Squares function minimized: (SHELXL Version 2014/7); $\Sigma w(F_o^2 - F_c^2)^2$ where w=Least Squares weights) on $F^2$ was based on 12008 observed reflections and 849 variable parameters and converged (largest parameter shift was 0.00 times its esd) with unweighted and weighted agreement factors of:

$$R1 = \Sigma ||Fo| - |Fc|| / \Sigma |Fo| = 0.0522$$

$$wR2 = [\Sigma(w(Fo^2 - Fc^2)^2) / \Sigma w(Fo^2)^2]^{1/2} = 0.1632$$

The goodness of fit was 1.45. Goodness of fit is defined as: $[\Sigma w(Fo2-Fc2)2/(No-Nv)]^{1/2}$, where: $N_o$=number of observations and Nv=number of variables.

Unit weights were used. The maximum and minimum peaks on the final difference Fourier map corresponded to 1.79 and −0.69 $e^-/Å^3$, respectively. The final Flack parameter was 0.029(7), indicating that the structure is inversion-twin. (Parsons, S. and Flack, H. (2004), *Acta Cryst.* A60, s61; Flack, H. D. and Bernardinelli (2000), *J. Appl. Cryst.* 33, 114-1148).

Neutral atom scattering factors were taken from International Tables for Crystallography (IT), Vol. C, Table 6.1.1.4. (International Tables for Crystallography, Vol. C (1992). Ed. A. J. C. Wilson, Kluwer Academic Publishers, Dordrecht, Netherlands, Table 6.1.1.4, pp. 572). Anomalous dispersion effects were included in Fcalc (Ibers, J. A. & Hamilton, W. C.; Acta Crystallogr., 17, 781 (1964)); the values for Δf and Δf" were those of Creagh and McAuley. (Creagh, D. C. & McAuley, W. J.; "International Tables for Crystallography", Vol C, (A. J. C. Wilson, ed.), Kluwer Academic Publishers, Boston, Table 4.2.6.8, pages 219-222 (1992)). The values for the mass attenuation coefficients are those of Creagh and Hubbell. (Creagh, D. C. & Hubbell, J. H.; "International Tables for Crystallography", Vol C, (A. J. C. Wilson, ed.), Kluwer Academic Publishers, Boston, Table 4.2.4.3, pages 200-206 (1992)). All calculations were performed using the CrystalStructure crystallographic software package except for refinement, which was performed using SHELXL Version 2014/7. (CrystalStructure 4.2: Crystal Structure Analysis Package, Rigaku Corporation (2000-2015). Tokyo 196-8666, Japan; *SHELXL Version* 2014/7: Sheldrick, G. M. (2008). *Acta Cryst.* A64, 112-122).

Crystal data, intensity measurements, and structure solution and refinement were as shown below:

| A. Crystal Data | |
| --- | --- |
| Empirical Formula | $C_{22}H_{33}N_{10}O_7P$ |
| Formula Weight | 580.54 |
| Crystal Color, Habit | nONE, nONE |
| Crystal Dimensions | not described |
| Crystal System | monoclinic |
| Lattice Type | C-centered |
| No. of Reflections Used for Unit Cell Determination (2θ range) | 36473 (7.7-147.1°) |
| Omega Scan Peak Width at Half-height | 0.00° |
| Lattice Parameters | a = 33.3523(2) Å |
|  | b = 13.80020(11) Å |
|  | c = 14.19956(10) Å |
|  | β = 96.8075(6)° |
|  | V = 6489.53(8) Å$^3$ |
| Space Group | C2 (#5) |
| Z value | 4 |
| $D_{calc}$ | 0.594 g/cm$^3$ |
| $F_{000}$ | 1224.00 |
| μ(CuKα) | 6.011 cm$^{-1}$ |

| B. Intensity Measurements | |
| --- | --- |
| Diffractometer | CuKα (λ = 1.54187 Å) |
| Radiation | graphite monochromated |
| Take-off Angle | 2.8° |
| Detector Aperture | 2.0-2.5 mm horizontal |
|  | 2.0 mm vertical |
| Crystal to Detector Distance | 21 mm |
| Temperature | 23.0° C. |
| Scan Type | ω-2θ |
| Scan Rate | 0.0°/min (in ω) (up to 0 scans) |
| Scan Width | (0.00 + 0.00 tan θ)° |
| $2θ_{max}$ | 147.7° |
| No. of Reflections Measured | Total: 50795 |
|  | Unique: 12008 ($R_{int}$ = 0.0453) |
|  | Parsons quotients (Flack x parameter): 4813 |
| Corrections | Lorentz-polarization |
|  | Absorption |
|  | (trans. factors: 0.341-1.000) |

| C. Structure Solution and Refinement | |
| --- | --- |
| Structure Solution | Direct Methods (SHELXT Version 2014/5) |
| Refinement | Full-matrix least-squares on $F^2$ |
| Function Minimized | $\Sigma w (Fo^2 - Fc^2)^2$ |
| Least Squares Weights | w = 1/[σ$^2$(Fo$^2$) + (0.1000 · P)$^2$ + 0.0000 · P] |
|  | where P = (Max(Fo$^2$, 0) + 2Fc$^2$)/3 |
| $2θ_{max}$ cutoff | 147.7° |
| Anomalous Dispersion | All non-hydrogen atoms |
| No. Observations (All reflections) | 12008 |
| No. Variables | 849 |
| Reflection/Parameter Ratio | 14.14 |
| Residuals: R1 (I > 2.00σ(I)) | 0.0522 |
| Residuals: R (All reflections) | 0.0534 |
| Residuals: wR2 (All reflections) | 0.1632 |
| Goodness of Fit Indicator | 1.450 |
| Flack parameter (Parsons' quotients = 4813) | 0.029(7) |
| Max Shift/Error in Final Cycle | 0.001 |
| Maximum peak in Final Diff. Map | 1.79 e$^-$/Å$^3$ |
| Minimum peak in Final Diff. Map | −0.69 e$^-$/Å$^3$ |

[$^1$H-NMR data for Compound 100]

$^1$H NMR (400 MHz, D$_2$O) δ 8.25 (s, 1H), 8.15 (s, 1H), 7.40 (s, 1H), 5.85 (d, 1H), 5.45 (d, 1H), 4.25 (m, 2H), 4.05 (m, 1H), 3.85 (m, 1H), 3.6 (m, 2H), 3.4 (m, 4H), 2.90 (m, 4H), 2.60 (d, 6H), 1.8 (s, 3H).

All documents mentioned in this application are incorporated by reference herein. If there is any discrepancy between the incorporated document and this document, then this document controls.

We claim:

1. A method for preparing an oligomer represented by the formula:

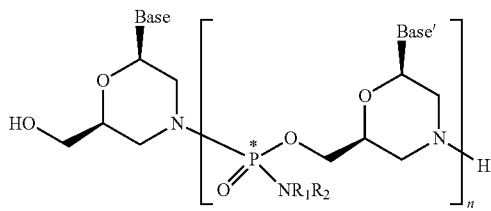

wherein:

Base is selected from the group consisting of:

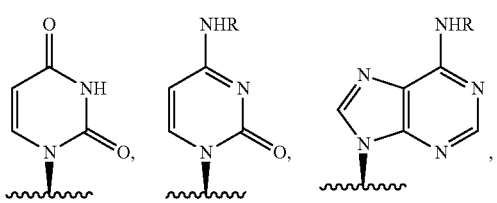

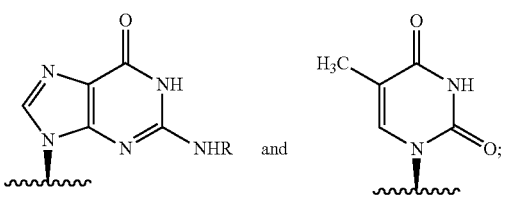

each Base' is independently selected from the group consisting of:

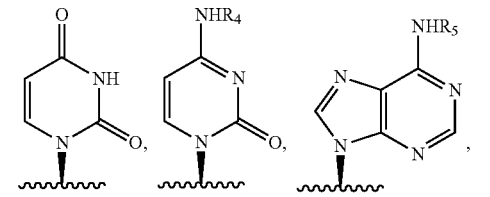

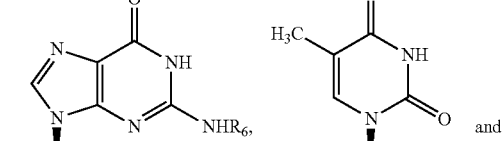

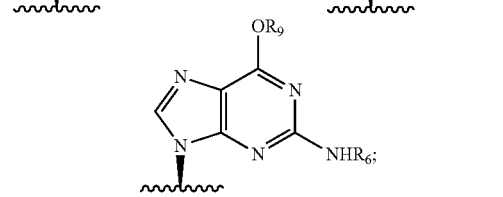

each R is independently selected from H, C(O)R$_7$ or C(O)OR$_7$;

each R$_1$ is independently selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;

each R$_2$ is independently selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;

each R$_4$ is independently selected from H, C(O)R$_7$ or C(O)OR$_7$;

each R$_5$ is independently selected from H, C(O)R$_7$ or C(O)OR$_7$;

41 each $R_6$ is independently selected from H, $C(O)R_7$ or $C(O)OR_7$;

each $R_7$ is independently selected from $C_1$-$C_6$ alkyl or aryl, where the aryl is optionally substituted with a substituent selected from the group consisting of halogen, nitro and methoxy;

each $R_9$ is independently selected from alkyl, acyl, sulfonyl, carbonate, carbamate, benzyl or silyl, wherein the alkyl is optionally substituted with cyano, and further wherein the benzyl is optionally substituted with pivaloyloxy;

each * is independently (R) or (S); and n is 1, 2, 3, 4, 5, 6, 7, 8, 9, 10, 11, 12, 13, 14 or 15;

comprising the following steps:

1) reacting a tert-butyldiphenylsilyl-protected morpholino monomer selected from the group consisting of:

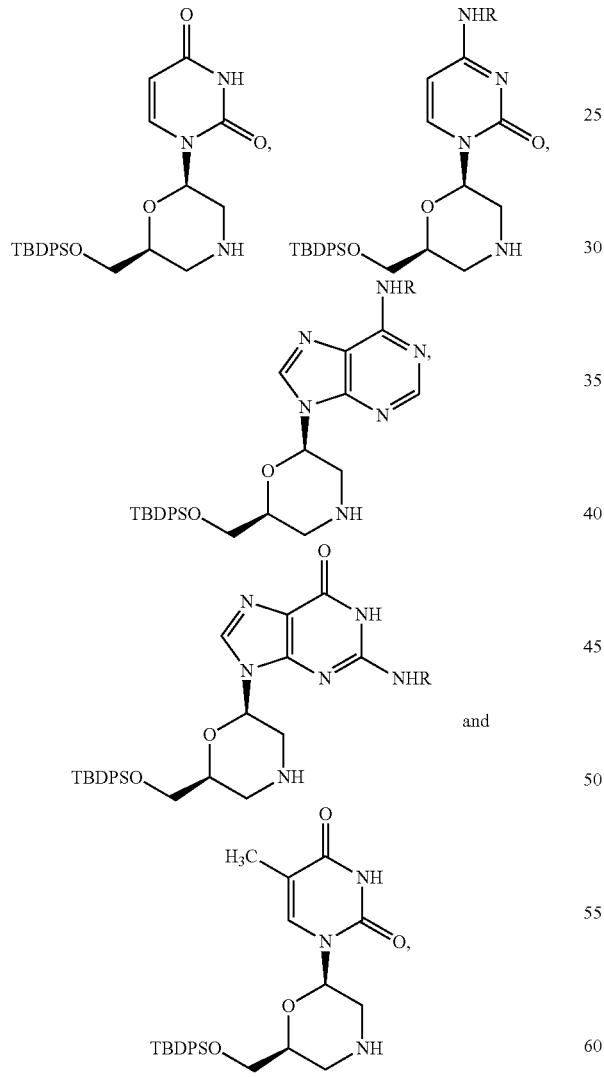

wherein:

R is selected from H, $C(O)R_7$ or $C(O)OR_7$;

$R_7$ is selected from $C_1$-$C_6$ alkyl or aryl, where the aryl is optionally substituted with a substituent

42 selected from the group consisting of halogen, nitro and methoxy; and

TBDPS is tert-butyldiphenylsilyl;

with a phosphoramidochloridate morpholino monomer selected from the group consisting of Formula 20, Formula 21, Formula 22, Formula 23, Formula 24, Formula 25, Formula 26, Formula 27, Formula 28, Formula 29, Formula 30 and Formula 31:

Formula 20

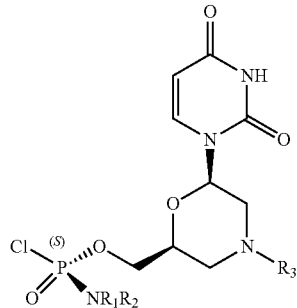

Formula 21

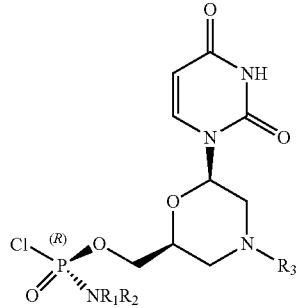

Formula 22

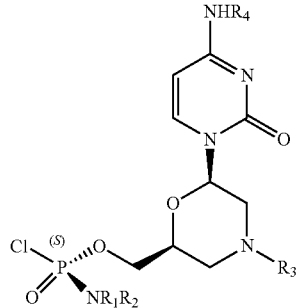

Formula 23

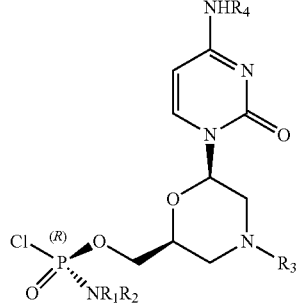

-continued

Formula 24
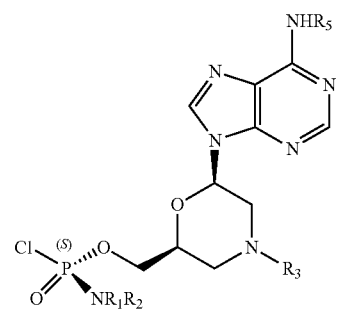

Formula 25
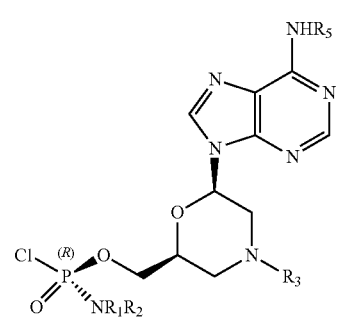

Formula 26
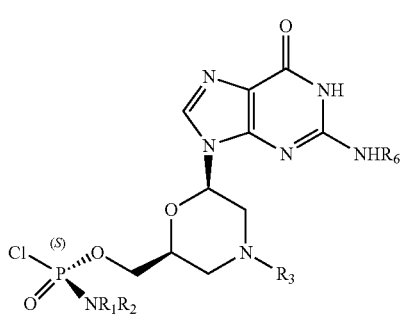

Formula 27
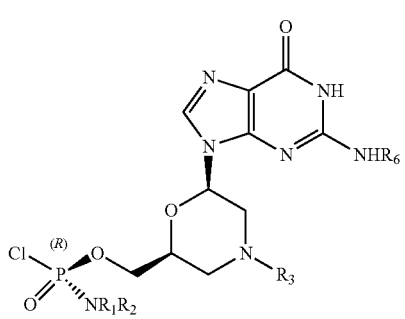

Formula 28
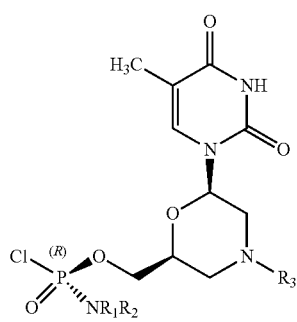

-continued

Formula 29
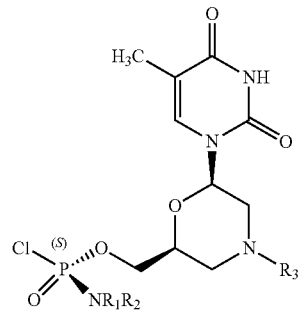

Formula 30
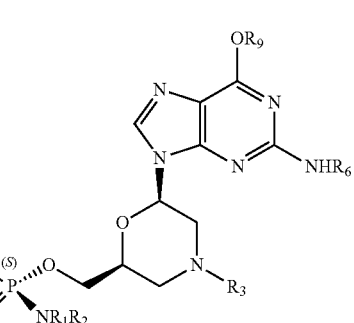

Formula 31
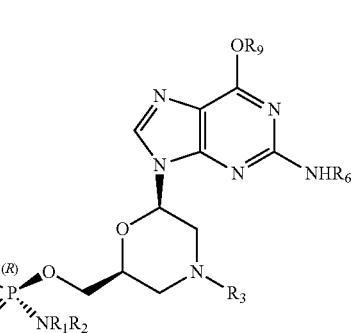

wherein:
- $R_1$ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
- $R_2$ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
- $R_3$ is selected from diphenylmethyl, triphenylmethyl or benzyl, where the phenyl portion of triphenylmethyl and benzyl is optionally substituted with one or more methoxy substituents;
- $R_4$ is selected from H, C(O)$R_7$ or C(O)O$R_7$;
- $R_5$ is selected from H, C(O)$R_7$ or C(O)O$R_7$;
- $R_6$ is selected from H, C(O)$R_7$ or C(O)O$R_7$;
- $R_7$ is selected from $C_1$-$C_6$ alkyl or aryl, where the aryl is optionally substituted with a substituent selected from the group consisting of halogen, nitro and methoxy; and
- $R_9$ is selected from alkyl, acyl, sulfonyl, carbonate, carbamate, benzyl or silyl, wherein the alkyl is optionally substituted with cyano, and further wherein the benzyl is optionally substituted with pivaloyloxy;
in the presence of N-ethyldiisopropylamine, to provide an oligomer of formula (Ia):

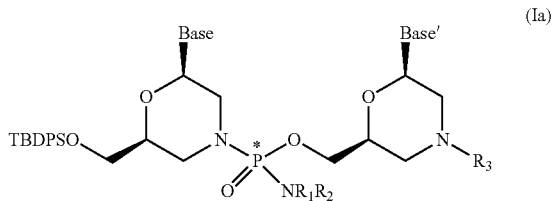

wherein:
Base is selected from the group consisting of:

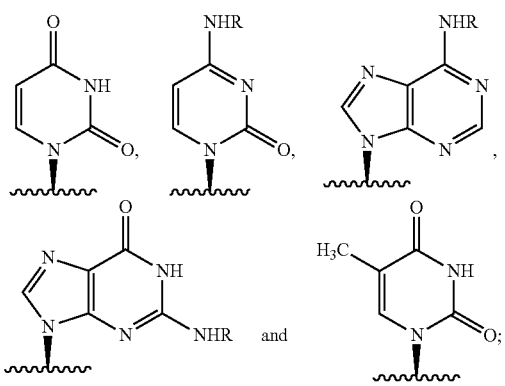

each Base' is independently selected from the group consisting of:

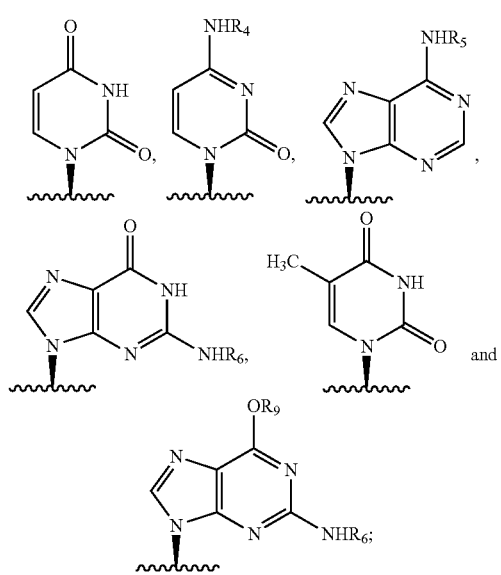

R is selected from H, C(O)R₇ or C(O)OR₇;
R₁ is selected from H, C₁-C₃ alkyl, phenyl or naphthyl, where the C₁-C₃ alkyl, phenyl and naphthyl are each optionally substituted with one or more substituents selected from the group consisting of halogen, nitro, cyano, methyl and ethyl;
R₂ is selected from H, C₁-C₃ alkyl, phenyl or naphthyl, where the C₁-C₃ alkyl, phenyl and naphthyl are each optionally substituted with one or more substituents selected from the group consisting of halogen, nitro, cyano, methyl and ethyl;
R₃ is selected from diphenylmethyl, triphenylmethyl or benzyl, where the phenyl portion of triphenylmethyl and benzyl is optionally substituted with one or more methoxy substituents;
R₄ is selected from H, C(O)R₇ or C(O)OR₇;
R₅ is selected from H, C(O)R₇ or C(O)OR₇;
R₆ is selected from H, C(O)R₇ or C(O)OR₇;
R₇ is selected from C₁-C₆ alkyl or aryl, where the aryl is optionally substituted with a substituent selected from the group consisting of halogen, nitro and methoxy;
* is (R) or (S); and
TBDPS is tert-butyldiphenylsilyl;
2) deprotecting the oligomer of formula (Ia) above with acetic acid, to provide an oligomer of formula (Ib):

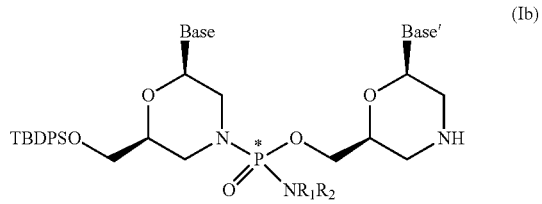

wherein:
Base is selected from the group consisting of:

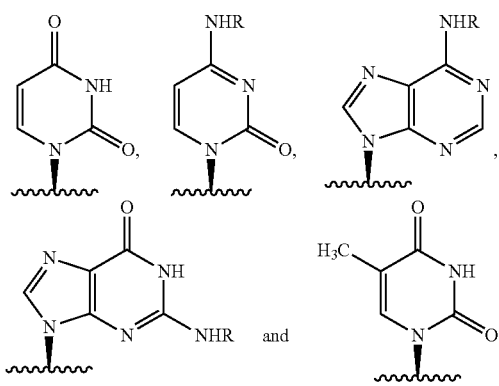

Base' is independently selected from the group consisting of:

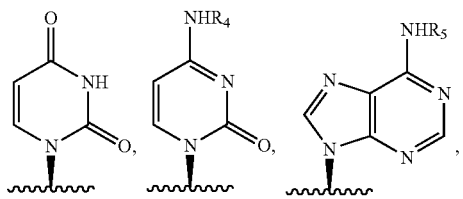

-continued

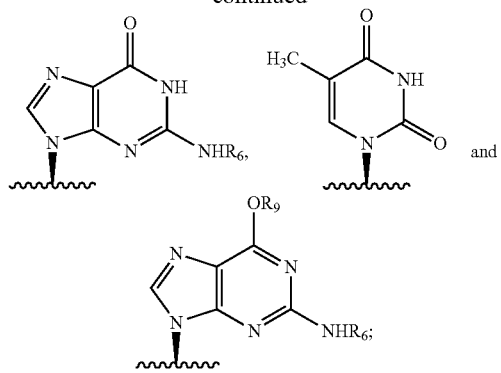

- R is selected from H, C(O)R$_7$ or C(O)OR$_7$;
- R$_1$ is selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;
- R$_2$ is selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;
- R$_4$ is selected from H, C(O)R$_7$ or C(O)OR$_7$;
- R$_5$ is selected from H, C(O)R$_7$ or C(O)OR$_7$;
- R$_6$ is selected from H, C(O)R$_7$ or C(O)OR$_7$;
- R$_7$ is selected from C$_1$-C$_6$ alkyl or aryl, where the aryl is optionally substituted with a substituent selected from the group consisting of halogen, nitro and methoxy;
- * is (R) or (S); and
- TBDPS is tert-butyldiphenylsilyl;

3) repeating step (a) and step (b) below 0, 1, 2, 3, 4, 5, 6, 7, 8, 9, 10, 11, 12, 13 or 14 times:
  (a) reacting the resulting oligomer with a phosphoramidochloridate morpholino monomer independently selected each time from the group consisting of Formula 20, Formula 21, Formula 22, Formula 23, Formula 24, Formula 25, Formula 26, Formula 27, Formula 28, Formula 29, Formula 30 and Formula 31 in the presence of N-ethyldiisopropylamine, to provide a N-protected 3-mer, 4-mer, 5-mer, 6-mer, 7-mer, 8-mer, 9-mer, 10-mer, 11-mer, 12-mer, 13-mer, 14-mer, 15-mer or 16-mer represented by the formula:

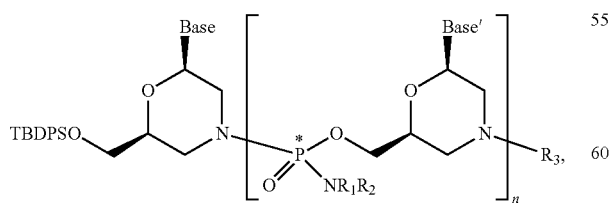

wherein:
each * is independently (R) or (S); and
n is 1, 2, 3, 4, 5, 6, 7, 8, 9, 10, 11, 12, 13, 14 or 15; and (b) deprotecting the oligomer of step (a) above with acetic acid, to provide an oligomer represented by the formula:

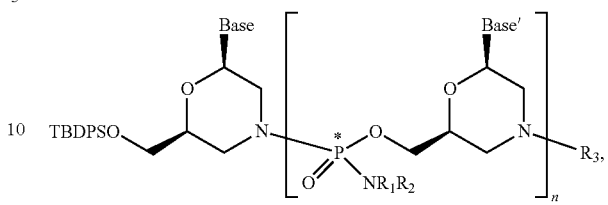

wherein:
* is independently (R) or (S); and
n is 1, 2, 3, 4, 5, 6, 7, 8, 9, 10, 11, 12, 13 or 14; and 4) deprotecting the oligomer of step 3) above with sodium hydroxide, to provide the oligomer represented by the formula:

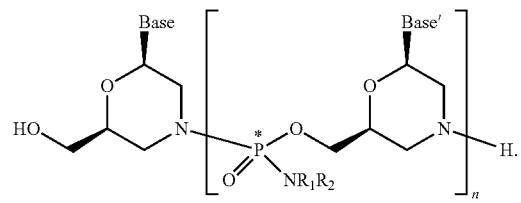

2. A method for preparing an oligomer represented by the formula:

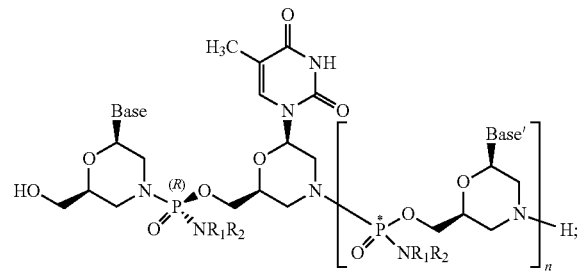

wherein:
Base is selected from the group consisting of:

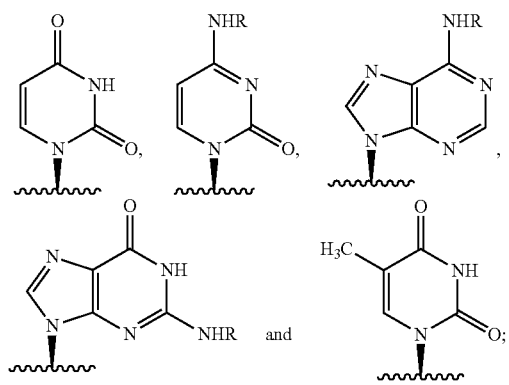

each Base' is independently selected from the group consisting of:

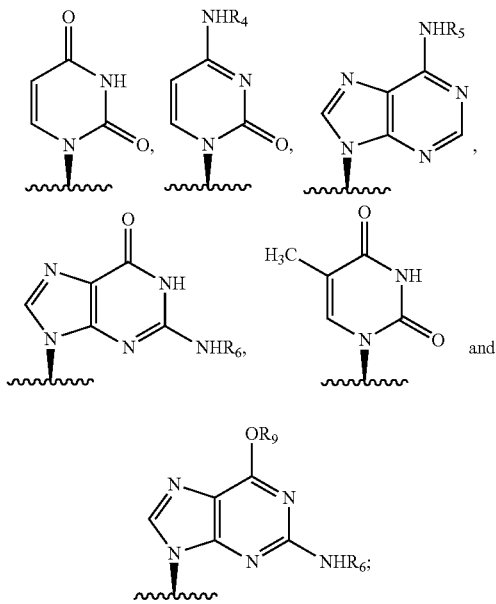

each R is independently selected from H, C(O)R$_7$ or C(O)OR$_7$;

each R$_1$ is independently selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;

each R$_2$ is independently selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;

each R$_4$ is independently selected from H, C(O)R$_7$ or C(O)OR$_7$;

each R$_5$ is independently selected from H, C(O)R$_7$ or C(O)OR$_7$;

each R$_6$ is independently selected from H, C(O)R$_7$ or C(O)OR$_7$;

each R$_7$ is independently selected from C$_1$-C$_6$ alkyl or aryl, where the aryl is optionally substituted with a substituent selected from the group consisting of halogen, nitro and methoxy;

each R$_9$ is independently selected from alkyl, acyl, sulfonyl, carbonate, carbamate, benzyl or silyl, wherein the alkyl is optionally substituted with cyano, and further wherein the benzyl is optionally substituted with pivaloyloxy;

each * is independently (R) or (S); and n is 1, 2, 3, 4, 5, 6, 7, 8, 9, 10, 11, 12, 13 or 14;

comprising the following steps:

1) reacting a tert-butyldiphenylsilyl-protected morpholino monomer selected from the group consisting of:

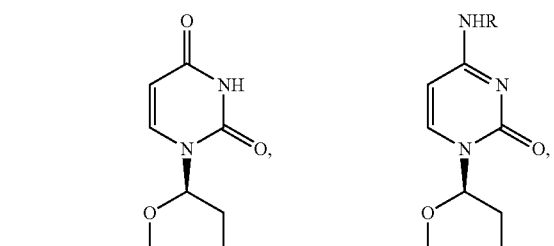

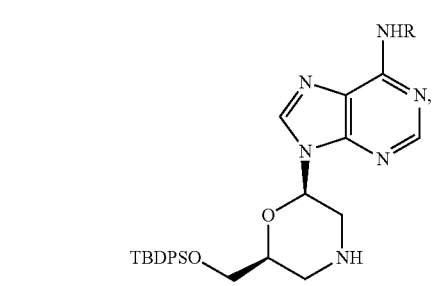

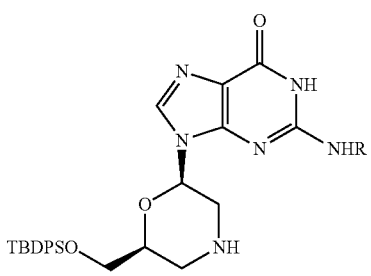

and

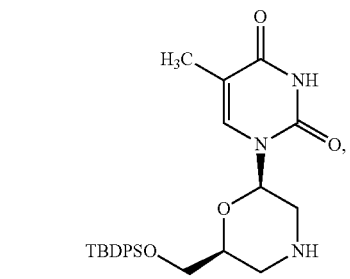

wherein:
R is selected from H, C(O)R$_7$ or C(O)OR$_7$;
R$_7$ is selected from C$_1$-C$_6$ alkyl or aryl, where the aryl is optionally substituted with a substituent selected from the group consisting of halogen, nitro and methoxy; and
TBDPS is tert-butyldiphenylsilyl;

with a phosphoramidochloridate morpholino monomer of Formula 28:

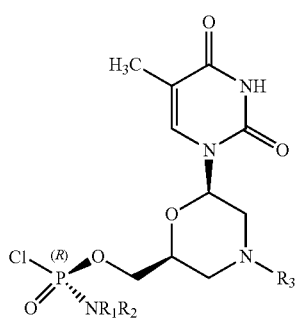

Formula 28 wherein:
- R₁ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
- R₂ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl; and
- R₃ is selected from diphenylmethyl, triphenylmethyl or benzyl, where the phenyl portion of triphenylmethyl and benzyl is optionally substituted with one or more methoxy substituents;

in the presence of N-ethyldiisopropylamine, to provide an oligomer of formula (Ia):

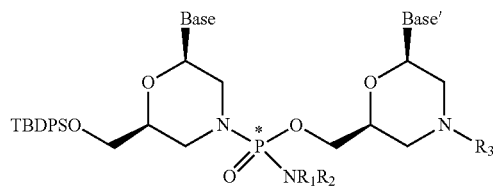

wherein:
Base is selected from the group consisting of:

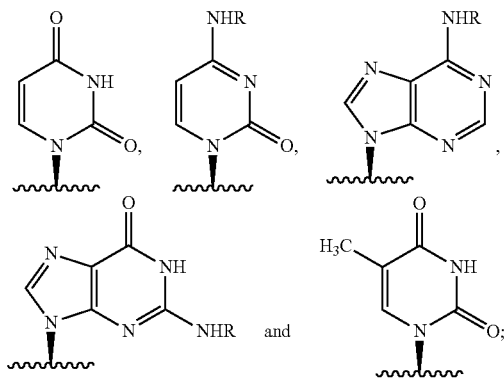

R is selected from H, C(O)R₇ or C(O)OR₇;
R₁ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₂ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₃ is selected from diphenylmethyl, triphenylethyl or benzyl, where the phenyl portion of triphenylmethyl and benzyl is optionally substituted with one or more methoxy substituents;
R₇ is selected from $C_1$-$C_6$ alkyl or aryl, where the aryl is optionally substituted with a substituent selected from the group consisting of halogen, nitro and methoxy; and
TBDPS is tert-butyldiphenylsilyl;

2) deprotecting the oligomer of formula (Ia) above with acetic acid, to provide an oligomer of formula (Ib):

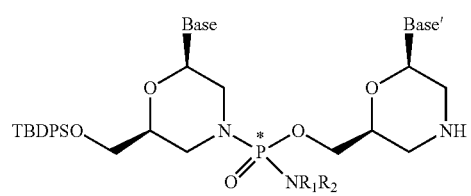

wherein:
Base is selected from the group consisting of:

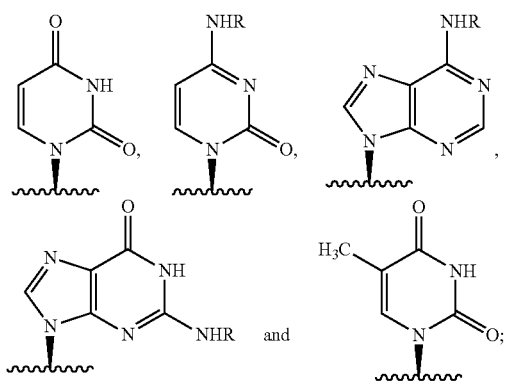

R is selected from H, C(O)R₇ or C(O)OR₇;
R₁ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₂ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₇ is selected from $C_1$-$C_6$ alkyl or aryl, where the aryl is optionally substituted with a substituent selected from the group consisting of halogen, nitro and methoxy; and TBDPS is tert-butyldiphenylsilyl; and 3) reacting the oligomer of formula (Ib) above with a phosphoramidochloridate morpholino monomer selected from the group consisting of Formula 20, Formula 21, Formula 22, Formula 23, Formula 24, Formula 25, Formula 26, Formula 27, Formula 28, Formula 29, Formula 30 and Formula 31:

Formula 20
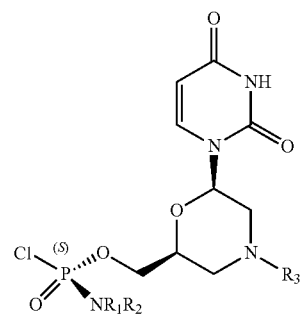

Formula 21
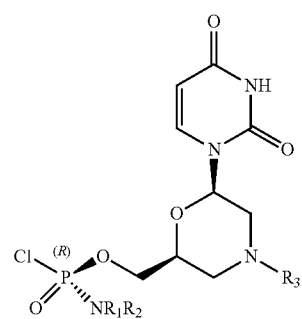

Formula 22
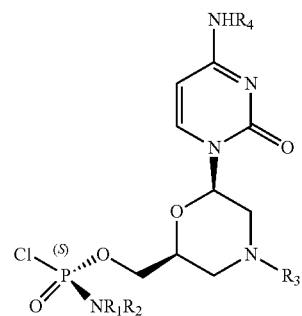

Formula 23
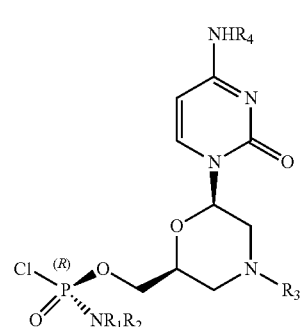

Formula 24
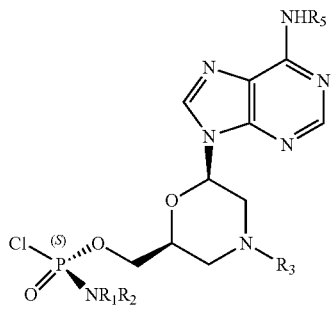

Formula 25
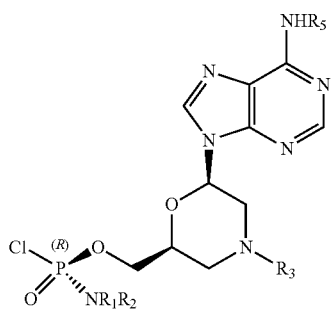

Formula 26
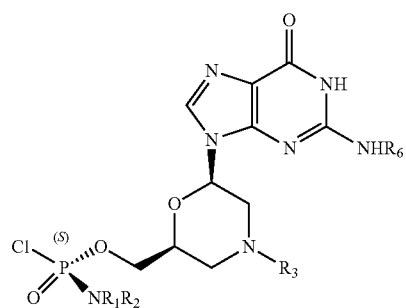

Formula 27
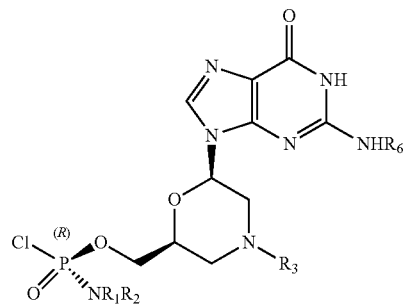

Formula 28
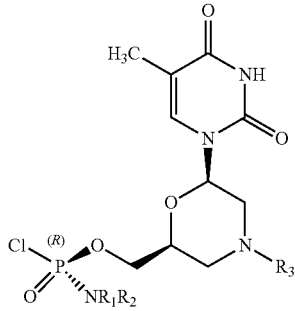

-continued

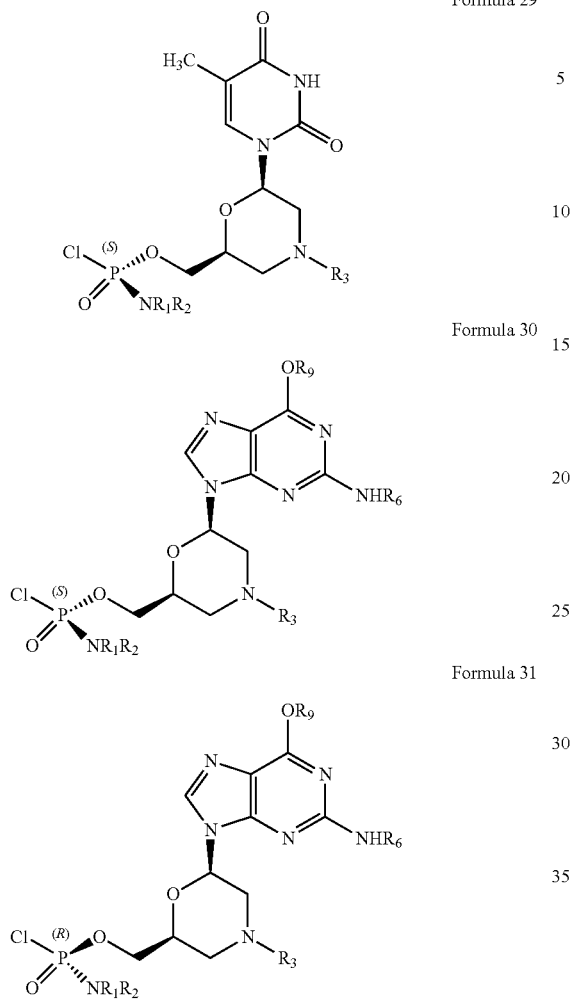

Formula 29

Formula 30

Formula 31 wherein:
R$_1$ is selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;
R$_2$ is selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;
R$_3$ is selected from diphenylmethyl, triphenylmethyl or benzyl, where the phenyl portion of triphenylmethyl and benzyl is optionally substituted with one or more methoxy substituents;
R$_4$ is selected from H, C(O)R$_7$ or C(O)OR$_7$;
R$_5$ is selected from H, C(O)R$_7$ or C(O)OR$_7$;
R$_6$ is selected from H, C(O)R$_7$ or C(O)OR$_7$;
R$_7$ is selected from C$_1$-C$_6$ alkyl or aryl, where the aryl is optionally substituted with a substituent selected from the group consisting of halogen, nitro and methoxy; and
R$_9$ is selected from alkyl, acyl, sulfonyl, carbonate, carbamate, benzyl or silyl, wherein the alkyl is optionally substituted with cyano, and further wherein the benzyl is optionally substituted with pivaloyloxy;
in the presence of N-ethyldiisopropylamine, to provide an oligomer represented by the formula:

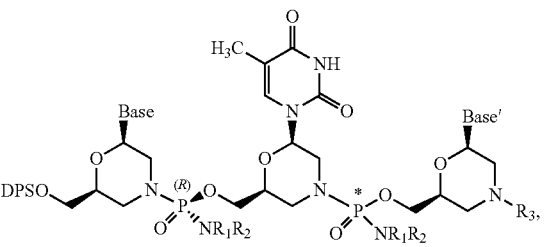

wherein:
Base is selected from the group consisting of:

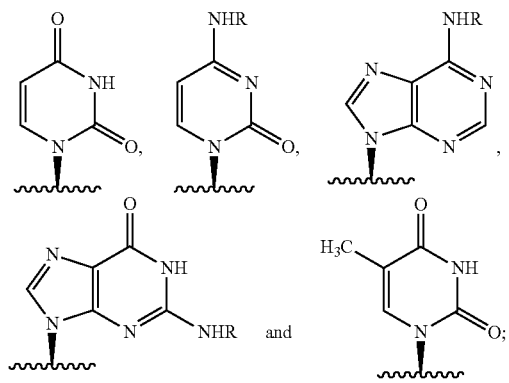

Base' is independently selected from the group consisting of:

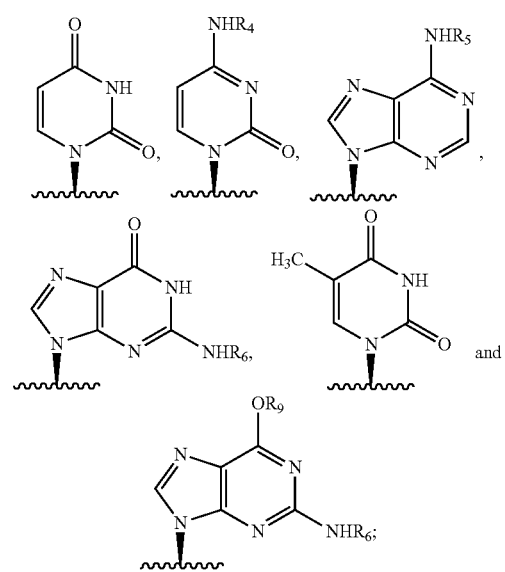

each R is independently selected from H, C(O)R$_7$ or C(O)OR$_7$;
each R$_1$ is independently selected from H, C$_1$-C$_3$ alkyl, phenyl or naphthyl, where the C$_1$-C$_3$ alkyl, phenyl and naphthyl are each optionally substituted with one or more substituents selected from the group consisting of halogen, nitro, cyano, methyl and ethyl;

each $R_2$ is independently selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;

$R_3$ is selected from diphenylmethyl, triphenylmethyl or benzyl, where the phenyl portion of triphenylmethyl and benzyl is optionally substituted with one or more methoxy substituents;

$R_4$ is selected from H, C(O)$R_7$ or C(O)O$R_7$;

$R_5$ is selected from H, C(O)$R_7$ or C(O)O$R_7$;

$R_6$ is selected from H, C(O)$R_7$ or C(O)O$R_7$;

$R_7$ is selected from $C_1$-$C_6$ alkyl or aryl, where the aryl is optionally substituted with a substituent selected from the group consisting of halogen, nitro and methoxy;

$R_9$ is selected from alkyl, acyl, sulfonyl, carbonate, carbamate, benzyl or silyl, wherein the alkyl is optionally substituted with cyano, and further wherein the benzyl is optionally substituted with pivaloyloxy;

\* is (R) or (S); and

TBDPS is tert-butyldiphenylsilyl;

4) deprotecting the oligomer of step 3) above with acetic acid, to provide an oligomer represented by the formula:

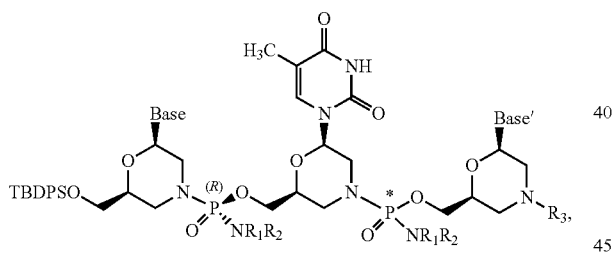

wherein:

Base is selected from the group consisting of:

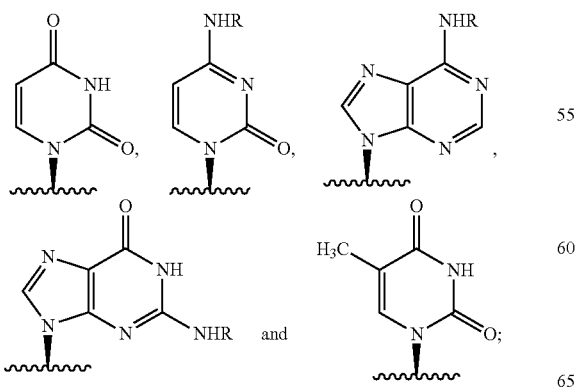

Base' is independently selected from the group consisting of:

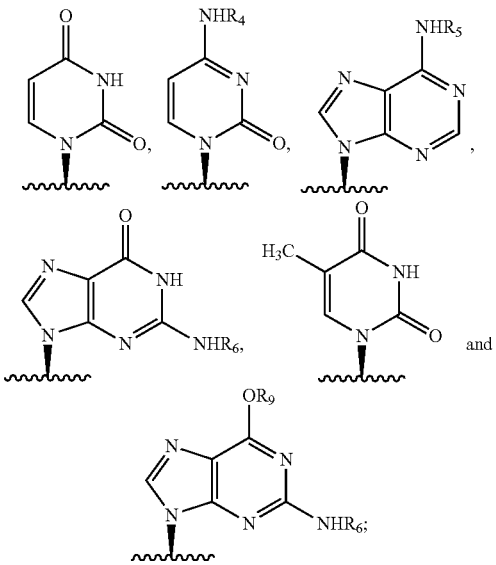

each R is independently selected from H, C(O)$R_7$ or C(O)O$R_7$;

each $R_1$ is independently selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;

each $R_2$ is independently selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;

$R_3$ is selected from diphenylmethyl, triphenylmethyl or benzyl, where the phenyl portion of triphenylmethyl and benzyl is optionally substituted with one or more methoxy substituents;

$R_4$ is selected from H, C(O)$R_7$ or C(O)O$R_7$;

$R_5$ is selected from H, C(O)$R_7$ or C(O)O$R_7$;

$R_6$ is selected from H, C(O)$R_7$ or C(O)O$R_7$;

$R_7$ is selected from $C_1$-$C_6$ alkyl or aryl, where the aryl is optionally substituted with a substituent selected from the group consisting of halogen, nitro and methoxy;

$R_9$ is selected from alkyl, acyl, sulfonyl, carbonate, carbamate, benzyl or silyl, wherein the alkyl is optionally substituted with cyano, and further wherein the benzyl is optionally substituted with pivaloyloxy; and \* is (R) or (S); and 5) repeating step (a) and step (b) below 0, 1, 2, 3, 4, 5, 6, 7, 8, 9, 10, 11, 12 or 13 times:

(a) reacting the resulting oligomer with a phosphoramidochloridate morpholino monomer independently selected each time from the group consisting of Formula 20, Formula 21, Formula 22, Formula 23, Formula 24, Formula 25, Formula 26, Formula 27, Formula 28, Formula 29, Formula 30 and Formula 31 in the presence of N-ethyldiisopropylamine, to provide a N-protected 3-mer, 4-mer, 5-mer, 6-mer, 7-mer, 8-mer, 9-mer, 10-mer, 11-mer, 12-mer, 13-mer, 14-mer, 15-mer or 16-mer represented by the formula:

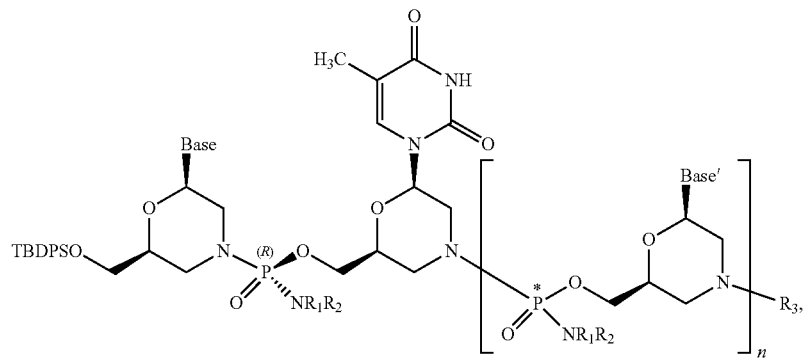

wherein:
each * is independently (R) or (S); and
n is 1, 2, 3, 4, 5, 6, 7, 8, 9, 10, 11, 12, 13 or 14; and (b) deprotecting the oligomer of step (a) above with acetic acid, to provide an oligomer represented by the formula:

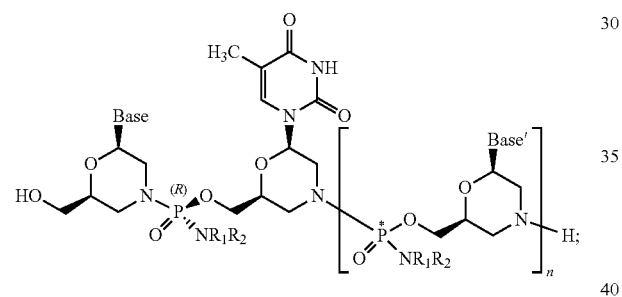

wherein:
each * is independently (R) or (S); and
n is 1, 2, 3, 4, 5, 6, 7, 8, 9, 10, 11, 12, 13 or 14; and 6) deprotecting the oligomer of step 5) above with sodium hydroxide, to provide the oligomer represented by the formula:

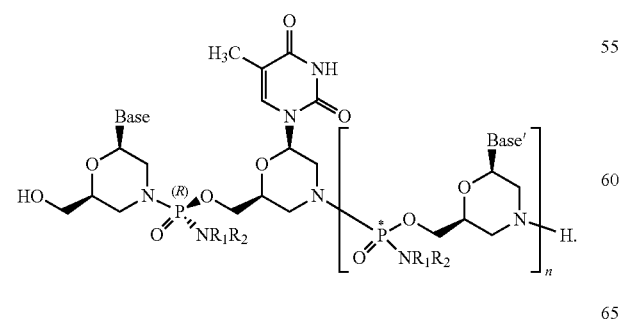

3. A method for preparing an oligomer of formula (I) or formula (II):

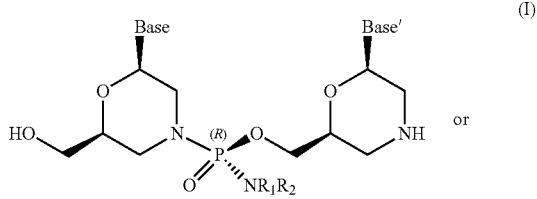

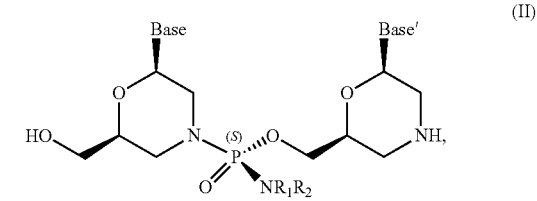

wherein:
Base is selected from the group consisting of:

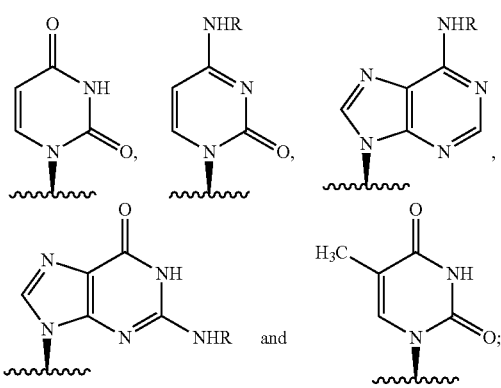

Base' is selected from the group consisting of:

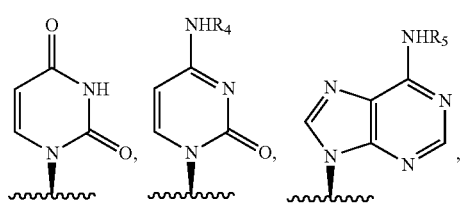

-continued

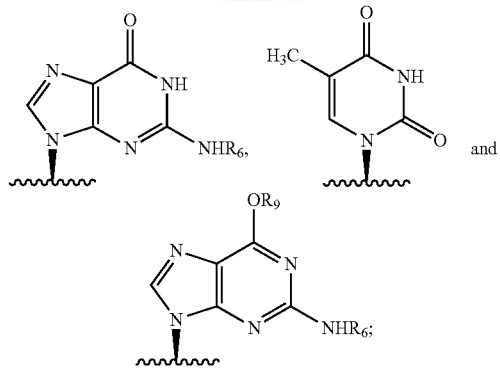

each R is independently selected from H, C(O)R₇ or C(O)OR₇;
R₁ is selected from H, C₁-C₃ alkyl, phenyl or naphthyl, where the C₁-C₃ alkyl, phenyl and naphthyl are each optionally substituted with one or more substituents selected from the group consisting of halogen, nitro, cyano, methyl and ethyl;
R₂ is selected from H, C₁-C₃ alkyl, phenyl or naphthyl, where the C₁-C₃ alkyl, phenyl and naphthyl are each optionally substituted with one or more substituents selected from the group consisting of halogen, nitro, cyano, methyl and ethyl;
R₄ is selected from H, C(O)R₇ or C(O)OR₇;
R₅ is selected from H, C(O)R₇ or C(O)OR₇;
R₆ is selected from H, C(O)R₇ or C(O)OR₇;
each R₇ is independently selected from C₁-C₆ alkyl or aryl, where the aryl is optionally substituted with a substituent selected from the group consisting of halogen, nitro and methoxy; and
R₉ is selected from alkyl, acyl, sulfonyl, carbonate, carbamate, benzyl or silyl, wherein the alkyl is optionally substituted with cyano, and further wherein the benzyl is optionally substituted with pivaloyloxy;
comprising the following steps:
1) reacting a tert-butyldiphenylsilyl-protected morpholino monomer selected from the group consisting of:

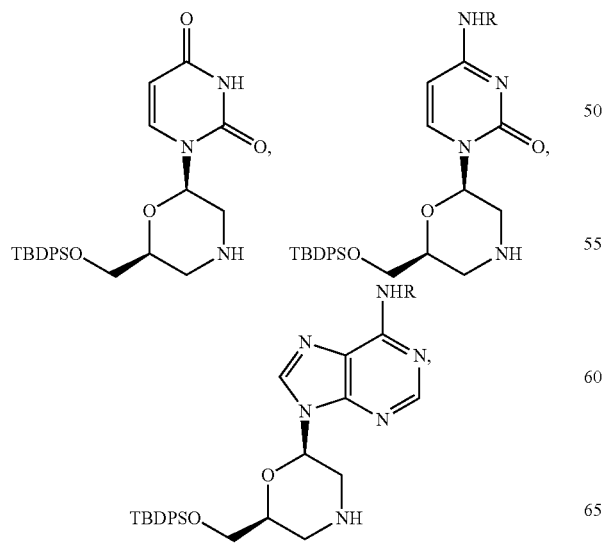

-continued

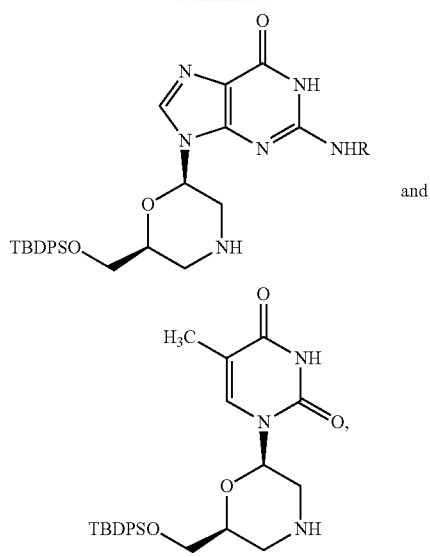

wherein:
R is selected from H, C(O)R₇ or C(O)OR₇;
R₇ is selected from C₁-C₆ alkyl or aryl, where the aryl is optionally substituted with a substituent selected from the group consisting of halogen, nitro and methoxy; and
TBDPS is tert-butyldiphenylsilyl;
with a phosphoramidochloridate morpholino monomer selected from the group consisting of Formula 20, Formula 21, Formula 22, Formula 23, Formula 24, Formula 25, Formula 26, Formula 27, Formula 28, Formula 29, Formula 30 and Formula 31:

Formula 20

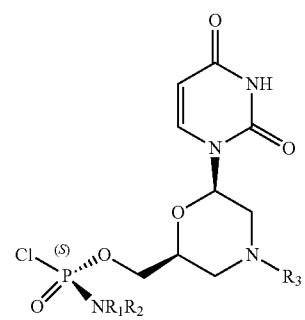

Formula 21

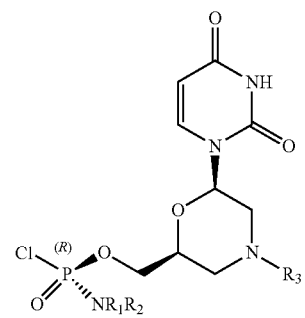

-continued
Formula 22
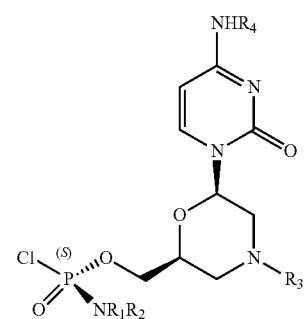
Formula 23
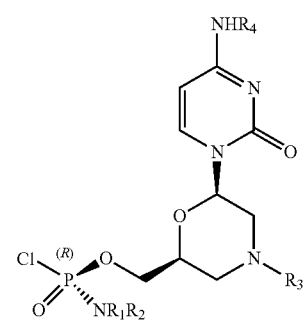
Formula 24
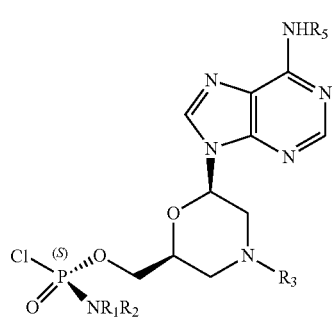
Formula 25
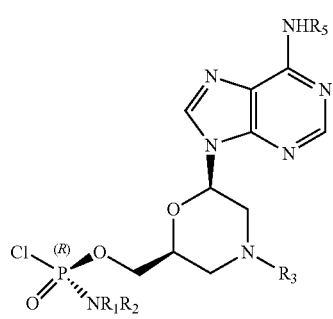
Formula 26
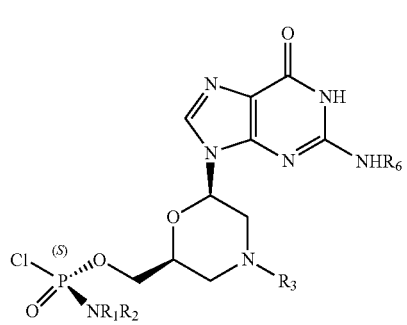
-continued
Formula 27
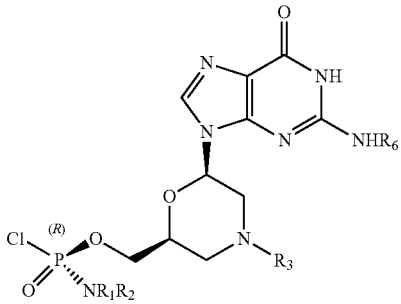
Formula 28
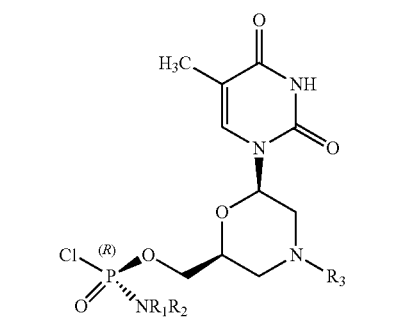
Formula 29
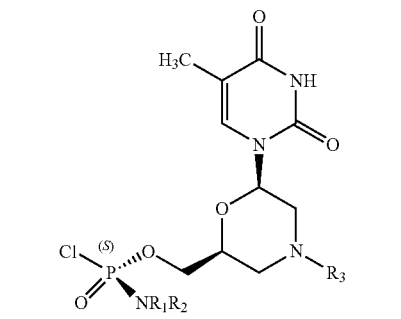
Formula 30
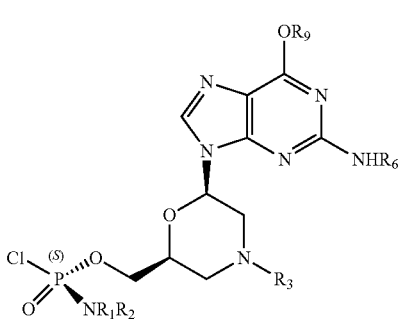
Formula 31
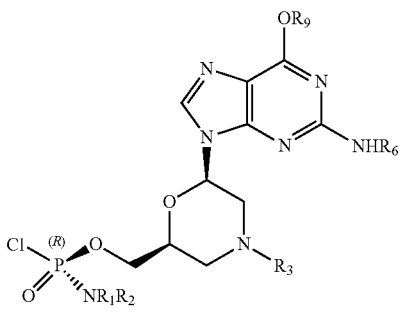

wherein:
- R₁ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
- R₂ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
- R₃ is selected from diphenylmethyl, triphenylmethyl or benzyl, where the phenyl portion of triphenylmethyl and benzyl is optionally substituted with one or more methoxy substituents;
- R₄ is selected from H, C(O)R₇ or C(O)OR₇;
- R₅ is selected from H, C(O)R₇ or C(O)OR₇;
- R₆ is selected from H, C(O)R₇ or C(O)OR₇;
- R₇ is selected from $C_1$-$C_6$ alkyl or aryl, where the aryl is optionally substituted with a substituent selected from the group consisting of halogen, nitro and methoxy; and
- R₉ is selected from alkyl, acyl, sulfonyl, carbonate, carbamate, benzyl or silyl, wherein the alkyl is optionally substituted with cyano, and further wherein the benzyl is optionally substituted with pivaloyloxy;

in the presence of N-ethyldiisopropylamine, to provide an oligomer of formula (Ia) or formula (IIa):

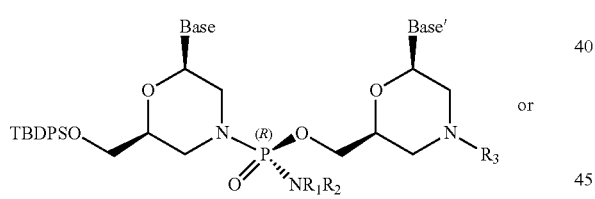
(Ia)

or

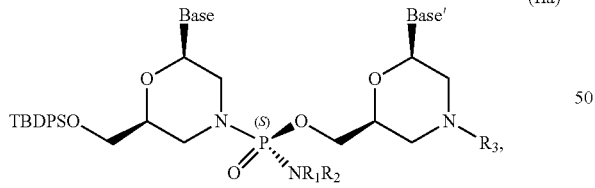
(IIa)

wherein:
Base is selected from the group consisting of:

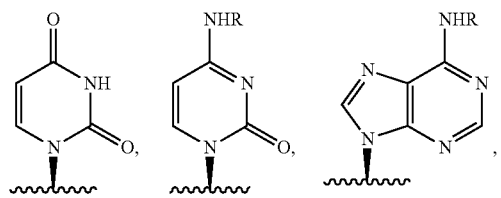

-continued

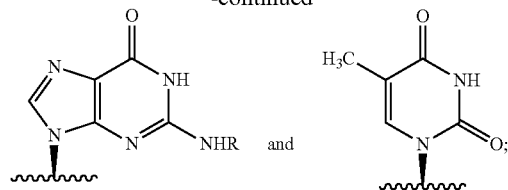

Base' is selected from the group consisting of:

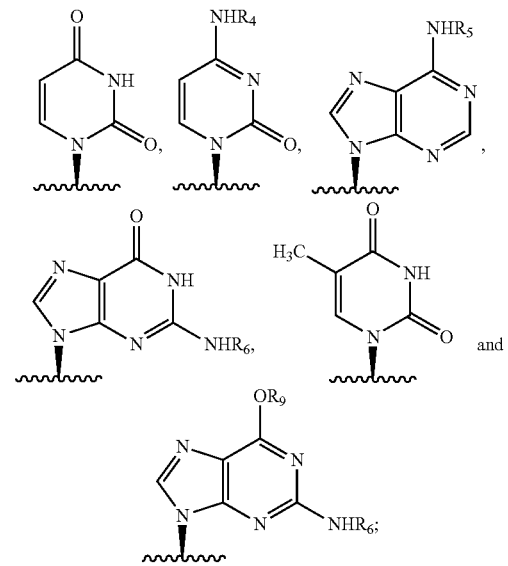

each R is independently selected from H, C(O)R₇ or C(O)OR₇;
R₁ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₂ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;
R₃ is selected from diphenylmethyl, triphenylmethyl or benzyl, where the phenyl portion of triphenylmethyl and benzyl is optionally substituted with one or more methoxy substituents;
R₄ is selected from H, C(O)R₇ or C(O)OR₇;
R₅ is selected from H, C(O)R₇ or C(O)OR₇;
R₆ is selected from H, C(O)R₇ or C(O)OR₇;
each R₇ is independently selected from $C_1$-$C_6$ alkyl or aryl, where the aryl is optionally substituted with a substituent selected from the group consisting of halogen, nitro and methoxy;
R₉ is selected from alkyl, acyl, sulfonyl, carbonate, carbamate, benzyl or silyl, wherein the alkyl is optionally substituted with cyano, and further wherein the benzyl is optionally substituted with pivaloyloxy; and
TBDPS is tert-butyldiphenylsilyl;

2) deprotecting the oligomer of formula (Ia) or formula (IIa) above with acetic acid, to provide an oligomer of formula (Ib) or formula (IIb):

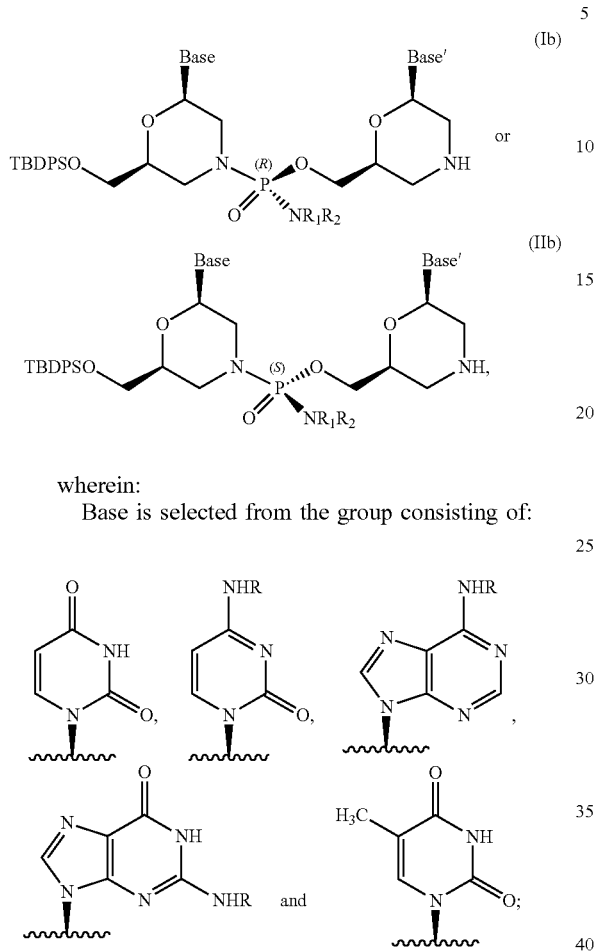

wherein:
Base is selected from the group consisting of:

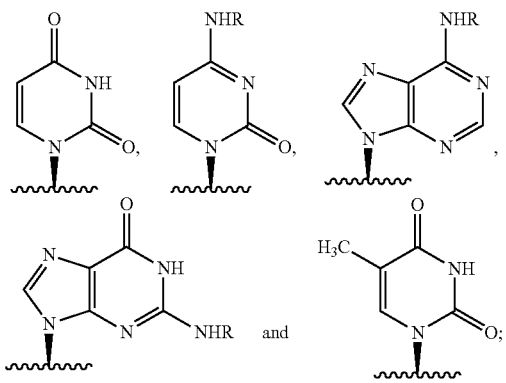

Base' is selected from the group consisting of:

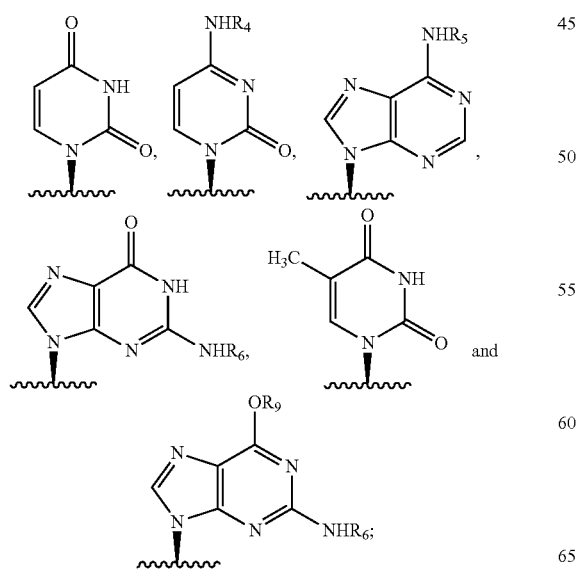

each R is independently selected from H, $C(O)R_7$ or $C(O)OR_7$;

$R_1$ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;

$R_2$ is selected from H, $C_1$-$C_3$ alkyl, phenyl or naphthyl, where the $C_1$-$C_3$ alkyl, phenyl and naphthyl are each optionally substituted with one or more substituents selected from the group consisting of halogen, nitro, cyano, methyl and ethyl;

$R_4$ is selected from H, $C(O)R_7$ or $C(O)OR_7$;

$R_5$ is selected from H, $C(O)R_7$ or $C(O)OR_7$;

$R_6$ is selected from H, $C(O)R_7$ or $C(O)OR_7$;

each $R_7$ is independently selected from $C_1$-$C_6$ alkyl or aryl, where the aryl is optionally substituted with a substituent selected from the group consisting of halogen, nitro and methoxy;

$R_9$ is selected from alkyl, acyl, sulfonyl, carbonate, carbamate, benzyl or silyl, wherein the alkyl is optionally substituted with cyano, and further wherein the benzyl is optionally substituted with pivaloyloxy; and TBDPS is tert-butyldiphenylsilyl; and 3) deprotecting the oligomer of formula (Ib) or formula (IIb) above with sodium hydroxide, to provide the oligomer of formula (I) or formula (II):

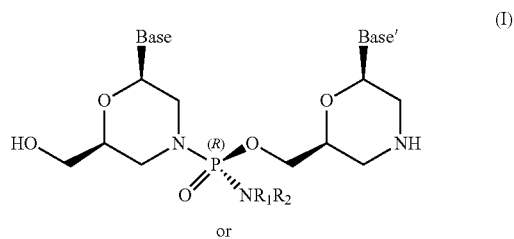

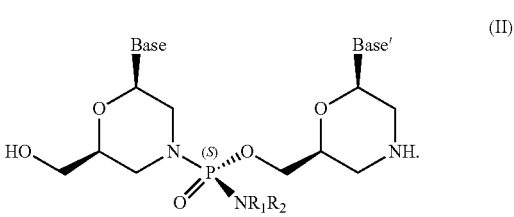

4. The method of claim 3, wherein the oligomer is Compound 100:

Compound 100
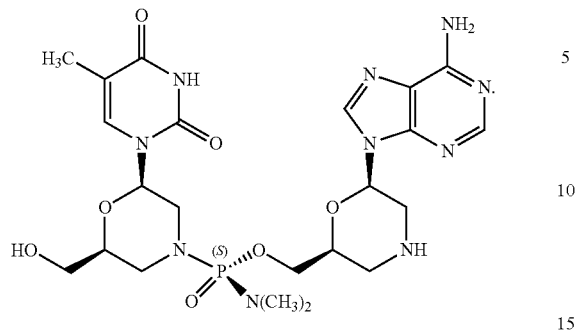
* * * * *

SEQUENCE LISTING

<160> NUMBER OF SEQ ID NOS: 2

<210> SEQ ID NO 1
<211> LENGTH: 16
<212> TYPE: RNA
<213> ORGANISM: Artificial Sequence
<220> FEATURE:
<223> OTHER INFORMATION: complimentary RNA sequence created for melting
      point analysis

<400> SEQUENCE: 1
uuccuugaug uuggag                                                16

<210> SEQ ID NO 2
<211> LENGTH: 16
<212> TYPE: DNA
<213> ORGANISM: Artificial Sequence
<220> FEATURE:
<223> OTHER INFORMATION: test sequence for synthesis, including
      unnatural linkage and nonstandard morpholine ring

<400> SEQUENCE: 2
ctccaacatc aaggaa                                                16